US008889731B2

(12) United States Patent
Gries et al.

(10) Patent No.: US 8,889,731 B2
(45) Date of Patent: Nov. 18, 2014

(54) COMPOUNDS, COMPOSITIONS AND METHODS FOR REPELLING BLOOD-FEEDING ARTHROPODS AND DETERRING THEIR LANDING AND FEEDING

(75) Inventors: Regine M. Gries, Coquitlam (CA); Gerhard G. Gries, Coquitlam (CA); Grigori Khaskin, Coquitlam (CA); Norman Avelino, Richmond (CA); Cory Campbell, Winnipeg (CA)

(73) Assignee: Contech Enterprises Inc., Victoria, CA (US)

( * ) Notice: Subject to any disclaimer, the term of this patent is extended or adjusted under 35 U.S.C. 154(b) by 1193 days.

(21) Appl. No.: 12/057,960

(22) Filed: Mar. 28, 2008

(65) Prior Publication Data
US 2009/0069407 A1    Mar. 12, 2009

Related U.S. Application Data

(60) Provisional application No. 60/908,481, filed on Mar. 28, 2007.

(51) Int. Cl.
| *A01N 43/18* | (2006.01) |
| *C07C 323/12* | (2006.01) |
| *A61Q 17/02* | (2006.01) |
| *C07C 321/20* | (2006.01) |
| *A61K 8/49* | (2006.01) |
| *A01N 43/28* | (2006.01) |
| *C07C 321/18* | (2006.01) |
| *C07D 335/02* | (2006.01) |
| *A01N 43/24* | (2006.01) |
| *A01N 31/02* | (2006.01) |
| *A01N 43/32* | (2006.01) |
| *A01N 41/12* | (2006.01) |
| *A61K 8/46* | (2006.01) |
| *C07C 321/28* | (2006.01) |

(52) U.S. Cl.
CPC ........... *C07D 335/02* (2013.01); *C07C 323/12* (2013.01); *A61Q 17/02* (2013.01); *C07C 321/20* (2013.01); *A61K 8/4986* (2013.01); *A01N 43/28* (2013.01); *C07C 321/18* (2013.01); *A01N 43/24* (2013.01); *A01N 31/02* (2013.01); *A01N 43/32* (2013.01); *A01N 41/12* (2013.01); *A61K 8/46* (2013.01); *C07C 321/28* (2013.01)
USPC ............. 514/432; 514/617; 514/713; 549/13; 564/183; 568/55; 568/60

(58) Field of Classification Search
None
See application file for complete search history.

(56) References Cited

U.S. PATENT DOCUMENTS

| 1,471,344 A | 10/1923 | Loudin |
| 1,871,949 A | 8/1932 | Bottrell |
| 1,911,551 A | 5/1933 | Cleveland |
| 1,995,247 A | 3/1935 | Haring |
| 2,213,156 A | 8/1940 | Granett |
| 2,254,665 A | 9/1941 | Ralston et al. |
| 2,273,860 A | 2/1942 | Granett |
| 2,302,159 A | 11/1942 | Wasum |
| 2,274,267 A | 2/1944 | Granett |
| 2,389,427 A | 11/1945 | Gertler |
| 2,396,012 A | 3/1946 | Jones et al. |
| 2,404,698 A | 7/1946 | Dreyling |
| 2,407,205 A | 9/1946 | Wilkes |
| 2,408,389 A | 10/1946 | Gertler |
| 2,435,780 A | 2/1948 | Heal |
| 2,469,228 A | 5/1949 | Gertler |
| 2,469,303 A | 5/1949 | Killingsworth |
| 2,512,675 A | 6/1950 | Pijoan et al. |
| 2,564,665 A | 8/1951 | Bartlett |
| 2,792,328 A | 5/1957 | Socec |
| 2,808,359 A | 10/1957 | Schmutzler |
| 2,863,799 A | 12/1958 | Goodhue |
| 2,884,355 A | 4/1959 | Goodhue et al. |

(Continued)

FOREIGN PATENT DOCUMENTS

BE       903756 A      6/1986
FR       2779615 A1    12/1999

(Continued)

OTHER PUBLICATIONS

Zhan, Z., and K. Lang. 2004. One-pot Synthetic Method of Allyl Sulfides: Samarium-induced Allyl Bromide Mediated Reduction of Alkyl Thiocyanates and Diaryl Disulfides in Methanolic Medium. Chemistry Letters; vol. 33(10): 1370-1371.*
Shin, HS, GM Strasburg, and JI Gray. 2002. A Model System Study of the Inhibition of Heterocyclic Aromatic Amine Formation by Organosulfur Compounds. J. Agric. Food Chem.; 50: 7684-7690.*

(Continued)

*Primary Examiner* — Carlos Azpuru
*Assistant Examiner* — David Browe
(74) *Attorney, Agent, or Firm* — Oyen Wiggs Green & Mutala LLP

(57) ABSTRACT

This invention relates to compositions of one or more compounds that incorporate one or more allyl sulfide, allyl disulfide or allyl polysulfide moieties, or one or more allyl sulfide, allyl disulfide or allyl polysulfide moieties and one or more hydroxyl groups, used in effective amount in formulations, including emulsions, to repel blood-feeding ectoparasitic arthropods, including mosquitoes, and to deter them from landing and feeding when applied to the skin, clothing or environment of animals, including humans. Said compounds can include, but are not limited to, 8-allyl-sulfanyloctan-1-ol. This invention also relates to compositions comprising one or more of said compounds in further combination with other arthropod repellent and deterrent compounds, including vanillin. These compounds may be formulated with inert ingredients to form a liquid, gel, paste, soap, spray, aerosol or powder.

23 Claims, 11 Drawing Sheets

(56) References Cited

U.S. PATENT DOCUMENTS

| | | |
|---|---|---|
| 2,937,969 A | 5/1960 | Bruce |
| 2,971,881 A | 2/1961 | Bruce |
| 2,991,219 A | 7/1961 | Bruce |
| 2,991,220 A | 7/1961 | Bruce |
| 3,067,093 A | 12/1962 | Goodhue et al. |
| 3,234,081 A | 2/1966 | Baker et al. |
| 3,406,177 A | 10/1968 | Yoho |
| 3,557,293 A | 1/1971 | Kashin et al. |
| 3,590,118 A | 6/1971 | Conrady et al. |
| 3,631,196 A | 12/1971 | Klosowski |
| 3,657,261 A | 4/1972 | Joos et al. |
| 3,707,541 A | 12/1972 | Lajiness |
| 3,825,555 A | 7/1974 | Lajiness |
| 3,953,477 A | 4/1976 | Baker et al. |
| 3,975,541 A | 8/1976 | Bordenca et al. |
| 4,028,411 A | 6/1977 | Baker et al. |
| 4,054,576 A | 10/1977 | Baker et al. |
| 4,064,268 A | 12/1977 | Adolphi et al. |
| RE29,829 E | 11/1978 | Bordenca et al. |
| 4,127,672 A | 11/1978 | Klier et al. |
| 4,164,561 A | 8/1979 | Hautmann |
| 4,219,570 A | 8/1980 | Inazuka et al. |
| 4,264,594 A | 4/1981 | McGovern et al. |
| 4,291,041 A | 9/1981 | McGovern et al. |
| 4,298,612 A | 11/1981 | McGovern et al. |
| 4,299,840 A | 11/1981 | Skinner et al. |
| 4,303,675 A | 12/1981 | Di Pietro et al. |
| 4,348,400 A | 9/1982 | Wong |
| 4,356,180 A | 10/1982 | McGovern et al. |
| 4,357,336 A | 11/1982 | Wong |
| 4,382,950 A | 5/1983 | McGovern et al. |
| 4,389,401 A | 6/1983 | Smolanoff |
| 4,393,068 A | 7/1983 | Wong |
| 4,407,807 A | 10/1983 | Wong |
| 4,416,881 A | 11/1983 | McGovern et al. |
| 4,419,360 A | 12/1983 | Smolanoff |
| 4,427,700 A | 1/1984 | Retnakaran |
| 4,457,934 A | 7/1984 | Wong |
| 4,466,967 A | 8/1984 | Smolanoff |
| 4,477,467 A | 10/1984 | Nishizawa et al. |
| 4,547,360 A | 10/1985 | Perlberg |
| 4,554,277 A | 11/1985 | Wong |
| 4,555,515 A | 11/1985 | Wong |
| 4,579,850 A | 4/1986 | Wong |
| 4,612,327 A | 9/1986 | Matukuma et al. |
| 4,621,143 A | 11/1986 | McGovern et al. |
| 4,663,346 A | 5/1987 | Coulston et al. |
| 4,693,890 A | 9/1987 | Wilson et al. |
| 4,696,676 A | 9/1987 | Wilson et al. |
| 4,707,496 A | 11/1987 | Simmons |
| 4,774,081 A | 9/1988 | Flashinski et al. |
| 4,774,082 A | 9/1988 | Flashinski et al. |
| 4,797,408 A | 1/1989 | McGovern et al. |
| 4,804,683 A | 2/1989 | Steltenkamp |
| 4,816,256 A | 3/1989 | Randen |
| 4,869,896 A | 9/1989 | Coulston et al. |
| 4,873,252 A | 10/1989 | Kruger et al. |
| 4,876,090 A | 10/1989 | Weisler |
| 4,900,834 A | 2/1990 | Kruger et al. |
| 4,946,850 A | 8/1990 | Kruger et al. |
| 5,006,562 A | 4/1991 | Steltenkamp |
| 5,008,261 A | 4/1991 | Kruger et al. |
| 5,017,377 A | 5/1991 | Sikinami et al. |
| 5,091,423 A | 2/1992 | Wilson et al. |
| 5,106,622 A | 4/1992 | Sherwood et al. |
| 5,109,022 A | 4/1992 | Jeanne et al. |
| 5,118,711 A | 6/1992 | Wilson et al. |
| 5,126,369 A | 6/1992 | Wilson et al. |
| 5,130,136 A | 7/1992 | Shono et al. |
| 5,175,175 A | 12/1992 | Wilson et al. |
| 5,182,304 A | 1/1993 | Steltenkamp |
| 5,196,200 A | 3/1993 | Wilson et al. |
| 5,204,372 A | 4/1993 | Wilson et al. |
| 5,206,022 A | 4/1993 | Nichols |
| 5,208,029 A | 5/1993 | Plummer et al. |
| 5,227,163 A | 7/1993 | Eini et al. |
| 5,227,406 A | 7/1993 | Beldock et al. |
| 5,228,233 A | 7/1993 | Butler et al. |
| 5,250,575 A | 10/1993 | Wilson et al. |
| 5,258,408 A | 11/1993 | Steltenkamp |
| 5,272,179 A | 12/1993 | Butler et al. |
| 5,298,250 A | 3/1994 | Lett et al. |
| 5,344,847 A | 9/1994 | Wilson et al. |
| 5,346,922 A | 9/1994 | Beldock et al. |
| 5,354,783 A | 10/1994 | Marin et al. |
| 5,391,578 A | 2/1995 | Steltenkamp |
| 5,409,958 A | 4/1995 | Butler et al. |
| 5,411,992 A | 5/1995 | Eini et al. |
| 5,417,009 A | 5/1995 | Butler et al. |
| 5,429,817 A | 7/1995 | McKenzie |
| 5,434,189 A | 7/1995 | Steltenkamp |
| 5,434,190 A | 7/1995 | Steltenkamp |
| 5,441,988 A | 8/1995 | Butler et al. |
| 5,447,714 A | 9/1995 | Marin et al. |
| 5,449,695 A | 9/1995 | Marin et al. |
| 5,458,882 A | 10/1995 | Marin et al. |
| 5,472,701 A | 12/1995 | Warren et al. |
| 5,484,599 A | 1/1996 | Yoder et al. |
| 5,496,852 A | 3/1996 | Oliver |
| 5,521,165 A | 5/1996 | Warren et al. |
| 5,556,881 A | 9/1996 | Grahn Marisi |
| 5,565,208 A | 10/1996 | Vlasblom |
| 5,576,010 A | 11/1996 | Warren et al. |
| 5,576,011 A | 11/1996 | Butler et al. |
| 5,589,181 A | 12/1996 | Bencsits |
| 5,594,029 A | 1/1997 | Bencsits |
| 5,610,194 A | 3/1997 | Polefka et al. |
| 5,621,013 A | 4/1997 | Beldock et al. |
| 5,626,882 A | 5/1997 | Marrone et al. |
| 5,633,236 A | 5/1997 | Warren et al. |
| 5,648,398 A | 7/1997 | Beldock et al. |
| 5,653,991 A | 8/1997 | Rod |
| 5,665,781 A | 9/1997 | Warren et al. |
| 5,696,158 A | 12/1997 | Oliver |
| 5,698,209 A | 12/1997 | Shono et al. |
| 5,711,953 A | 1/1998 | Bassett |
| 5,716,602 A | 2/1998 | Uick |
| 5,721,274 A | 2/1998 | Vander Meer et al. |
| 5,733,552 A | 3/1998 | Anderson et al. |
| 5,753,686 A | 5/1998 | Marin et al. |
| 5,776,477 A | 7/1998 | Ryder |
| 5,792,467 A | 8/1998 | Emerson et al. |
| 5,798,385 A | 8/1998 | Marin |
| 5,814,325 A | 9/1998 | Rod |
| 5,855,903 A | 1/1999 | Warren et al. |
| 5,885,600 A | 3/1999 | Blum et al. |
| 5,900,243 A | 5/1999 | Yoder et al. |
| 5,925,371 A | 7/1999 | Ishiwatari |
| 5,929,113 A | 7/1999 | Manker et al. |
| 6,071,973 A | 6/2000 | Vander Meer et al. |
| 6,130,255 A | 10/2000 | Ikemoto et al. |
| 6,143,288 A | 11/2000 | Warren et al. |
| 6,180,127 B1 | 1/2001 | Calton et al. |
| 6,255,356 B1 | 7/2001 | Butler |
| 6,294,577 B1 | 9/2001 | Vander Meer et al. |
| 6,306,415 B1 | 10/2001 | Reifenrath |
| 6,355,264 B1 | 3/2002 | Garrison et al. |
| 6,362,235 B1 | 3/2002 | Nolen et al. |
| 6,372,804 B1 | 4/2002 | Ikemoto et al. |
| 6,437,001 B1 | 8/2002 | Roe |
| 6,444,216 B2 | 9/2002 | Reifenrath |
| 6,451,844 B1 | 9/2002 | Watkins et al. |
| 6,458,826 B2 | 10/2002 | Froelich et al. |
| 6,488,950 B1 | 12/2002 | Arand et al. |
| 6,511,674 B1 | 1/2003 | Arand et al. |
| 6,524,605 B1 | 2/2003 | Coats et al. |
| 6,538,027 B1 | 3/2003 | Manker et al. |
| 6,562,359 B2 | 5/2003 | Watanabe et al. |
| 6,562,841 B1 | 5/2003 | Klun et al. |
| 6,605,643 B1 | 8/2003 | Ross |
| 6,660,288 B1 | 12/2003 | Behan et al. |
| 6,676,955 B2 | 1/2004 | Kensek |
| 6,800,662 B2 | 10/2004 | Roe |
| 6,897,244 B2 | 5/2005 | Zhu et al. |

(56) References Cited

U.S. PATENT DOCUMENTS

| | | | |
|---|---|---|---|
| 6,906,108 | B2 | 6/2005 | Henderson et al. |
| 6,953,814 | B2 | 10/2005 | Reifenrath |
| 7,037,515 | B2 | 5/2006 | Kalafsky et al. |
| 7,115,286 | B2 | 10/2006 | Meredith |
| 7,144,591 | B2 | 12/2006 | Bencsits |
| 7,179,479 | B1 | 2/2007 | Ahn et al. |
| 7,201,926 | B2 | 4/2007 | Fried et al. |
| 7,232,844 | B2 | 6/2007 | Hallahan |
| 7,288,573 | B2 | 10/2007 | Roe |
| 2004/0223998 | A1 | 11/2004 | Iyer et al. |
| 2005/0112164 | A1 | 5/2005 | Lewey |
| 2006/0110472 | A1 | 5/2006 | Miron et al. |
| 2006/0235071 | A1 | 10/2006 | Cantrell et al. |
| 2007/0224232 | A1 | 9/2007 | Sherwood |

FOREIGN PATENT DOCUMENTS

| | | |
|---|---|---|
| FR | 2863144 A1 | 6/2005 |
| JP | 55049304 A2 | 4/1980 |
| WO | 2004/100971 A1 | 11/2004 |
| WO | 2005/055713 A2 | 6/2005 |
| WO | 2007/041885 A2 | 4/2007 |

OTHER PUBLICATIONS

Badolo et al. (2004) "Evaluation of the sensitivity of *Aedes aegypti* and *Anopheles gambiae* complex mosquitoes to two insect repellents: DEET and KBR 3023" Trop. Med. Int. Hlth. 9: 330-334.

Barnard et al. (2004) "Laboratory evaluation of mosquito repellents against *Aedes albopictus, Culex nigripalpus*, and *Ochlerotatus triseriatus* (Diptera: Culicidae)" J. Med. Entomol. 41: 726-730.

Bhuyan et al. (1974) "Repellent property of oil fraction of garlic, *Allium sativum* (Linn.)" Indian J. Exp. Biol. 12: 575-576.

Block, E. (1992) "The organosulfur chemistry of the genus *Allium*—implications for the organic chemistry of sulfur" Angew. Chem. Int. Ed. Engl. 31: 1135-1178.

Block et al. (1988) "Lipoxygenase inhibitors from essential oil of garlic. Markovnikov addition of the allyldithio radical to olefins" J. Am. Chem. Soc. 110: 7813-7827.

Cantrell et al. (2005) "Isolation and identification of mosquito bite deterrent terpenoids from leaves of American (*Callicarpa americana*) and Japanese (*Callicarpa japonica*) beautyberry" J. Agric. Food Chem. 53: 5948-5953.

Carroll et al. (2007) "Repellency of two terpenoid compounds isolated from *Callicarpa americana* (Lamiaceae) against *Ixodes scapularis* and *Amblyomma americanum* ticks" Exp. Appl. Acarol. 41: 215-224.

Carroll et al. (2006) "PMD, a registered botanical mosquito repellent with DEET-like efficacy" J. Am. Mosq. Cont. Assoc. 22: 707-514.

Trigg, J.K. (1996) "Evaluation of a eucalyptus-based repellent against *Anopheles* spp. in Tanzania" J. Am. Mosq. Contr. Assoc. 12: 243-246.

Fradin et al. (2002) "Comparative efficacy of insect repellents against mosquito bites" N. Engl. J. Med. 347: 13-18.

Trongtokit et al. (2005) "Comparative repellency of 38 essential oils against mosquito bites" Phytother. Res. 19: 303-309.

Hill et al. (2005) "Arthropod-borne diseases: vector control in the genomics era" Nature Rev. Microbiol. 3: 262-268.

Mackenzie et al. (2004) "Emerging flaviviruses: the spread and resurgence of *Japanese encephalitis* , West Nile and Dengue viruses" Nature Medicine 10: S98-S109.

Mairuhu et al. (2004) "Dengue: and arthropod-borne disease of global importance" Eur. J. Clin. Microbiol. Infect. Dis. 23: 425-433.

Malavige et al. (2004) "Dengue viral infections" Postgrad. Med. J. 80: 588-601.

Miot et al. (2004) "Comparative study of the topical effectiveness of the andiroba oil (*Carapa guianensis*) and DEET 50% as a repellent for *Aedes*" sp. Rev. Inst. Med. Trop. S. Paulo. 46: 253-256.

Pest Management Regulatory Agency, Health Canada (2002) "Personal insect repellents containing DEET (N,N-diethyl-m-toluamide and related compounds)" Re-evaluation Decision Document No. RRD2002-01. 41 pp.

Zwiebel et al. (2004) "Olfactory regulation of mosquito-host interactions" Insect Biochem. Mol. Biol. 34: 645-652.

Moore et al. (2006) "Plant based insect repellents. In: Insect repellents: principles, methods, and uses" CRC Press, Boca Raton, FL. 495 pp.

Rajan et al. (2005) "A double-blinded, placebo-controlled trial of garlic as a mosquito repellant: a preliminary study" Med. Vet Entomol. 19:84-89.

Zanotto et al. (1996) "Population dynamics of flaviviruses revealed by molecular phylogenies" Proc. Nat. Acad. Sci. USA. 93: 548-553.

Sutcliffe, J.E. (1994) "Sensory bases of attractancy: morphology of mosquito olfactory sensilla—a review" J. Am. Mosq. Contr. Assoc. 10: 309-315.

Takken et al. (1997) "Interactions between physical and olfactory cues in the host-seeking behaviour of mosquitoes: the role of relative humidity" Annals Trop. Med. Parasitol. 91: S119-S120.

Tawatsin et al. (2001) "Repellency of volatile oils from plants against three mosquito vectors" J. Vector Ecol. 26: 7-82.

World Health Organization (1996) "Report of the WHO informal consultation on the evaluation and testing of insecticides" CID/WHOPEWS/IC/ 96.1. p.69.

Amonkar, et al., Science, vol. 174, Dec. 24, 1971, pp. 1343-1344.

Dikland, et al., Rubber Chemistry and Technology, vol. 66, 1993, pp. 693-711 (CA Accession No. 1995:12985).

Nishiguchi, et al., Chemistry Letters, vol. 12, Dec. 2002, pp. 1254-1255 (CA Accession No. 2002:957979).

Zhan, et al., Chemistry Letters, vol. 33, Oct. 2004, pp. 1370-1371 (CA Accession No. 2004:848439).

Huang, et al., Jingxi Huagong, vol. 22, 2005, pp. 127-129 (CA Accession No. 2005:272467).

Choochote et al. (2007) "Repellent activity of selected essential oils against *Aedes aegypti*" Fitoterapia 78:359-364.

Harwood et al. (1979) "Entomology in human and animal health" 7th Ed. Macmillan, New York. 548 pp.

Roe et al. (2006) "Development of a novel all natural tick and insect repellent, BIOUD, as a DEET replacement and for use on cotton fabric" pp. 1006-1016. In: Proc. 2006 Beltwide Cotton Conf., San Antonio, TX—Jan. 3-6, 2006.

Tuetun et al. (2005 "Repellent properties of celery, *Apium graveolens* L., compared with commercial repellents, against mosquitoes under laboratory and field conditions" Trop. Med. Internat. Health 10: 1190-1198.

* cited by examiner

COMPOUNDS, COMPOSITIONS AND METHODS FOR REPELLING BLOOD-FEEDING ARTHROPODS AND DETERRING THEIR LANDING AND FEEDING

CROSS-REFERENCE TO RELATED APPLICATIONS

This application claims priority to U.S. Provisional Patent Application No. 60/908,481, filed 28 Mar. 2007 and entitled "NOVEL SEMIOCHEMICALS FOR REPELLING ECTOPARASITIC ARTHROPODS AND DETERRING THEIR LANDING AND FEEDING", which is hereby incorporated herein by reference.

FIELD OF THE INVENTION

This invention relates to compounds, compositions and methods for repelling blood-feeding ectoparasitic arthropods, and deterring their landing and feeding, by applying in one or more formulations compounds incorporating one or more allyl sulfide, allyl disulfide and/or allyl polysulfide moieties to the skin, clothing or environment of animals, including humans. It further relates to the group of repellent and deterrent compounds comprising allylsulfide aliphatic alcohols, to compositions comprising one or more allyl sulfide, allyl disulfide or allyl polysulfide moieties and one or more hydroxyl groups combined in a further composition with one or more additional compounds, and to formulations of said compositions as emulsions.

BACKGROUND OF THE INVENTION

Haematophagous insects and certain other blood-feeding arthropods are ubiquitous ectoparasites of animals, including humans. In so doing, blood-feeding ectoparasitic arthropods constitute a major source of annoyance to humans and other animals, and are vectors of many microbial diseases, as well as those caused by viruses and virus-like disease agents (Harwood and James 1979).

Blood-feeding arthropods that annoy man and animals through their biting and feeding activity, and often vector disease-causing pathogens, comprise members of numerous insect taxa, including, but not limited to: flies in the Families Culicidae, Tabanidae, Psychodidae, Simuliidae, Muscidae and Ceratopgonidae (Order Diptera), bugs in the Families Cimicidae and Reduviidae (Order Hemiptera), lice in the Orders Mallophaga and Anoplura, and fleas in the Order Siphonaptera, as well as non-insectan arthropods, particularly ticks and mites in the Order Acari (also known as Acarina).

An example of a significant annoyance to humans and a major vector of disease-causing pathogens is the yellow fever mosquito, *Aedes aegypti* (Diptera: Culicidae), an exceptionally resilient blood-feeding species that breeds in any small container of water (Malavige et al. 2004). Adults are highly domesticated, typically resting indoors in dwellings, thus optimizing their opportunity to feed and vector pathogens that cause diseases such as yellow fever and dengue fever (Mackenzie et al. 2004; Malavige et al. 2004; Hill et al. 2005). Annually, 7.2 million humans become infected with yellow fever, and >30,000 die from the disease. Moreover, 50-100 million humans are infected with dengue fever (500,000 with its henmorhagic form), resulting in approximately 24,000 deaths annually (Zanotto et al. 1996; Mairuhu et al. 2004). Other species of *Aedes*, as well as mosquitoes in other genera, particularly *Anopheles* and *Culex*, are also significant annoyance agents and vectors of disease-causing pathogens.

The most effective protection against mosquitoes and other ectoparasitic arthropods, is to repel them from, or deter their landing and feeding on, potential hosts. Until recently, the most efficacious known "repellent" was N,N-diethyl-m-toluamide (DEET) (Fradin and Day 2002). There are concerns associated with N,N-diethyl-m-toluamide. It is a solvent for some plastics, paints, varnishes and synthetic fabrics (Trigg 1996; Badolo et al. 2004; Miot et al. 2004). When used alone it may attract rather than repel *A. aegypti*. Finally, products exceeding 30% N,N-diethyl-m-toluamide are not recommended for protection of children (Pest Management Regulatory Agency 2002). Thus, there is a strong need for alternatives to N,N-diethyl-m-toluamide.

Research has led to several alternative repellents and deterrents to date (TABLE 1), some of them with efficacy equal to that of N,N-diethyl-m-toluamide (Barnard and Xue 2004). Many of these are natural compositions, and include essential oils from plants (cedar, rosemary, eucalyptus, andiroba, catnip, thyme, neem, clove, soybean) and grease or oils from animals. Active ingredients in some of these oils have been isolated and formulated in commercial products. OFF!® botanicals, for example, contain p-menthane-3,8-diol from lemon eucalyptus, *Eucalyptus maculata citriodon* (Beldock et al. 1997; Carroll and Loye 2006) as the active ingredient. Other new repellents for mosquitoes and other arthropods that are found in natural sources include: 2-undecanone (methyl nonyl ketone) from tomato plants (Roe 2002, 2004, 2007; Roe et al. 2006); tetrahydronootkatone (1,4,4a,5,6,7,8,10-octahydro-6-isopropyl-4,4a-dimethyl-2(1H)-naphthalenone) and 1,10-dihydronootkatone (1,4,4a,5,6,7,8,10-octahydro-6-isopropenyl-4,4a-dimethyl-2(1H)-naphthalenone) from yellow cedar (Zhu et al. 2005); and callicarpenal (13,14,15,16-tetranor-3-cleroden-12-al) and intermedeol [(4S,5S,7R,10S)-eudesm-11-en-4-ol] from American beautyberry (Cantrell et al. 2005, 2006; Carroll et al. 2007).

TABLE 1

Names, ingredients, and formulations of 13 representative mosquito repellents. Concentration of ingredients as stated on product label.
Names and ingredients Neem Aura: *Aloe vera*, extract of barberry, camomile, goldenseal, myrrh, neem, and thyme; oil of anise, cedary citronella, coconut, lavender, lemongrass, neem, orange, rhodiumwood. NeemAura Naturals, Inc., Alachua, FL
GonE!: *Aloe vera*, camphor, menthol, oils of eucalyptus, lavender, rosemary, sage, and soybean. Aubrey Organics, Tampa, FL
SunSwat: oils of bay, cedarwood, citronella, goldenseal, juniper, lavender, lemon peel, patchouli, pennyroyal, tea tree, and vetivert. Kiss My Face Corp., Gardiner, NY
Natrapel: citronella (10%). Tender Corp., Littleton, NH
Bygone: oils of canola, eucalyptus, peppermint, rosemary, and sweetbirch. Lakon Herbals, Inc., Montpelier, VT
Bite Blocker: glycerin, lecithin, vanillin, oils of coconut, geranium, and soybean (2%). Homs, LLC, Clayton, NC
BioUD8: undecanone (7.75%). Homs, LLC, Clayton, NC
Skinsations: N,N-diethyl-m-toluamide (7%). Spectrum Corp., St. Louis, MO
Off!: N,N-diethyl-m-toluamide (15%). S. C. Johnson & Sons, Inc., Racine, WI
Avon Skin-So-Soft Bug Guard plus IR3535: 3-(N-butyl-N-acetyl)-amino propionic acid, ethyl ester (7.5%). Avon Products, Inc., New York
Autan Active Insect Repellent: 1-(1-methyl-propoxycarbonyl)-2-(2-hydroxy-ethyl)-piperidine (Picaridin KBR-3023) (10%). Bayer Ltd., Dublin, Ireland
Repel: lemon eucalyptus insect repellent lotion. Oil of lemon eucalyptus (65% p-menthane-3,8-diol [PMD]). Wisconsin Pharmacal Co., Inc., Jackson, WI TABLE 1-continued Names, ingredients, and formulations of 13 representative mosquito repellents. Concentration of ingredients as stated on product label.
Names and ingredients MosquitoSafe: geraniol 25%, mineral oil 74%, *Aloe vera* 1%. Naturale Ltd., Great Neck, NY Many of the patented repellents and deterrents for arthropods are compositions. These are of two types: 1) compositions comprising a single active ingredient formulated with one or more inert ingredients that serve as a carrier or stabilizer, and 2) compositions of two or more active ingredients that provide an additive or synergistic effect on efficacy of the composition over that provided by any of the components alone. Compositions of the second type usually also have inert ingredients as formulants.

Examples of the first type of composition include: p-menthane-3,8-diol in ethylene/vinyl acetate co-polymer (Sikinami et al. 1991); N,N-diethyl-m-toluamide formulated in a liquefiable powder (Nichols 1993); garlic juice in filtered water (McKenzie 1995); carane-3,4-diol in a cellulose matrix (Ishiwateri 1999); and N,N-diethyl-n-toluamide formulated as an emulsion (Ross 2003).

Compounds used as additives with other repellents include, but are not limited to: vanillin, 1,8-cineole, linalool, citronellal, citronellol, camphor, menthone, isomenthone, menthol, borneol, isomenthol, α-terpineol, cis- and trans-piperitol, nerol, neral, cinnamaldehyde, cumin aldehyde, geraniol, geraniol, thymol, bornyl acetate, menthyl acetate, cumin alcohol, geranyl formate, geranyl acetate, caryophyllene, and cis-cinnamyl acetate. As indicated in some of the following examples, repellent additives are often combined with N,N-diethyl-m-toluamide to improve its efficacy.

Specific examples of the second type of composition include: 1,2,3,4-tetrahydro-β-naphthol and 2-phenyl cyclohexanol (Pijoan and Jachowski 1950); N,N-diethyl-m-toluamide and halobenzoylproprionate (1977, Dec. 20, U.S. Pat. No. 4,064,268); N,N-diethyl-m-toluamide, citral and citronella oil (Hautmaim 1979); oils of citronella, cedar, wintergreen and pennyroyal in an oleic acid carrier (Sherwood and Sherwood 1992); N,N-diethyl-m-toluamide and N-alkyl neotridecanamide (Polefka et al. 1997); p-menthane-3,8-diol, citronella, geraniol and α-terpineol (Beldock et al. 1997); geraniol, citronellol and nerol (Butler 2001); and N,N-diethyl-m-toluamide and dihydronepalactone (Hallahan 2007).

Vanillin has been shown to improve the repellence of N,N-diethyl-m-toluamide against black flies (Retnakaran 1984), and extracted oils of four species of plants (of 11 tested) against mosquitoes (Tuetun et al. 2005; Choochote et al. 2007). On the other hand, Fried et al. (2007) teach that "vanillin may be added as a stabilizer" in combination with a number of essential plant oils, but do not report any increase in repellence against flies and mosquitoes.

Garlic, *Allium sativum*, has well known antibacterial, antihelminthic and antitumor properties (Block 1992). It is also used with uncertain efficacy and understanding as an insect repellent. Bassett (1998) claims repellence of mosquitoes with a composition of garlic juice and hot pepper sauce, but does not reveal the contribution of each of these components. McKenzie (1995) describes a simple method of combining garlic juice and water to make a composition for repelling insects from fruit and vegetable plants. Arand and Arand (2002, 2003) improved on the methodology of McKenzie (1995), by developing a method of combining a measured amount of extract of a garlic puree with an inert carrier to form a composition of known concentration that is then added to a more conventional pesticide to improve its efficacy in a maimer that "is not totally understood at this time." Similarly, Anderson and Brock (1998) claim that spraying dilute garlic juice on a grassy area can repel mosquitoes for many months, for "reasons not wholly understood". Arand and Arand (2002, 2003) report improvements in the preparation of garlic extract and the use of said extract in composition with known insecticides.

Consumption of garlic as a means of repelling mosquitoes is widely practiced (Moore et al. 2006), but with no proven efficacy (Rajan et al. 2005). Weisler (1989) reports that administration of a 1:20 composition of aneurine (Vitamin $B_1$) and garlic oil in the diet of domesticated animals can protect them from ingestion by fleas and ticks. However, in a test with flea-infested dogs, neither component was effective alone, and Weisler (1989) did not disclose whether either aneurine or some component of garlic oil actually was present in the skin of the test dogs. Therefore, the actual role of both components is uncertain. Moreover, Weisler (1989) erroneously teaches that allyl sulfide is the same as garlic oil, when in fact garlic oil is a complex mixture of many compounds (see FIG. 1).

Topical application of pure garlic oil can also be used to repel mosquitoes. Such an application provided 70 minutes of protection against *A. aegypti* (Trongtokit et al. 2005). Similarly, garlic oil (1%) formulated in petroleum jelly and beeswax provided 8 hours of protection against *Culex fatigans* (Bhuyan et al. 1974).

No systematic experimental study has been done to determine the identity of potentially bio-active compounds in garlic and garlic oil. Therefore, the ingredients therein that express repellence and deterrence to blood-feeding insects and other blood-feeding arthropods are unknown.

SUMMARY OF THE INVENTION

In general terms this invention pertains to compounds found in garlic, or synthetic compounds of related structure, that incorporate one or more of allyl sulfide, allyl disulfide, and/or allyl polysulfide moieties, and one or more hydroxyl groups, and are used to repel blood-feeding ectoparasitic arthropods or deter their landing and feeding. Said blood-feeding arthropods can include, but are not limited to, ticks and mites in the Order Acari (also known as Acarina) and insects in the Orders Mallophaga, Anoplura, Siphonaptera, Hemiptera (Families Cimicidae and Reduviidae), and Diptera (Families Culicidae, Tabanidae, Psychodidae, Simuliidae, Muscidae and Ceratopogonidae). The dipteran insects in the family Culicidae can include, but are not limited to, species in the genera *Aedes, Culex, Anopheles, Chagasia, Bironella, Culiseta, Ochlerotatus, Psorophora, Toxorhynchites, Mansonia*, and *Coquillettidia*.

In specific terms said blood-feeding arthropod repellent and deterrent compounds can include, but are not limited to: methylallyl disulfide; [3H]-1,2-dithiolane; diallyl disulfide; methylallyl trisulfide; [4H]-1,2,3-trithiin; diallyl trisulfide; 5-methyl-1,2,3,4-tetrathiane; methylallyl tetrasulfide; [5H]-1,2,3,4-tetrathiepine; diallyl tetrasulfide; 4,5,9,10-tetrathiatrideca-1,12-diene; 6-methyl-4,5,8,9-tetrathiadodeca-1,11-diene; 2-(2,3-dithia-5-hexenyl)-3,4-dihydro-2(H)-thiopyran; 3-(2,3-dithia-5-hexenyl)-3,4-dihydro-2(H)-thiopyran; 1,2-bis-(1,2-dithia-4-pentenyl)-benzene; (E)-4,5-dithia-1,7-octadien-1-yl-benzene; trans-distyryldisulfide; 4,8-dithiaundeca-1,10-diene; 4,11-dithiatetradeca-1,13-diene; 4,13-dithiahexadeca-1,15-diene; and 4,12-dithiapentadeca-1,14-diene.

Additional blood-feeding ectoparasitic arthropod repellent and deterrent compounds can be saturated or unsaturated primary, secondary or tertiary alcohols with an allylsulfide, allyl disulfide or allyl polysulfide moiety, including, but not limited to: 9-allylsulfanylnonan-1-ol, 9-allylsulfanylnonan-2-ol, 8-allylsulfanyloctan-1-ol, 8-allylsulfanyloctan-2-ol, 8-allylsulfanyloctan-3-ol, 8-allylsulfanyloctan-4-ol, 7-allylsulfanylheptan-1-ol, 7-allylsulfanylheptan-2-ol, 6-allylsulfanylhexan-1-ol, and 6-allylsulfanylhexan-2-ol.

In a further aspect, this invention pertains to compositions comprising one or more compounds with one or more allyl sulfide, allyl disulfide, or allyl polysulfide moieties, and/or one or more hydroxyl groups, in combination with one or more additional blood-feeding arthropod repellent and deterrent compounds selected from the group including, but not limited to, the following: vanillin; 1,8-cineole; linalool; citronellal; citronellol; camphor; menthone; isomenthone; menthol; borneol; isomenthol; α-teipineol; cis- and trans-piperitol; nerol; neral; cinnamaldehyde; cumin aldehyde; geraniol; geranial; thymol; bornyl acetate; menthyl acetate; cumin alcohol; geranyl formate; geranyl acetate; caryophyllene; cis-cinnamyl acetate, N,N-diethyl-m-toluamide, p-menthane-3, 8-diol, 2-undecanone, tetrahydronootkatone, 1,10-dihydronootkatone, callicaipenal, and intermedeol.

In a final aspect, this invention pertains to methods of repelling blood feeding ectoparasitic arthropods, by applying said compositions of one or more compounds that incorporate one or more allyl sulfide, allyl disulfide, or allyl polysulfide moieties, and one or more hydroxyl groups, alone or in further compositions with one or more of said additional blood-feeding arthropod repellent and deterrent compounds, in effective amounts ranging from 1 nanogram to 100 milligrams per $cm^2$ of surface area in formulations, including emulsions, as a liquid, gel, paste, soap, spray, aerosol or powder to the skin, clothing or environment of an animal. Said animals can be an amphibian, reptile, bird or mammal, including a human. Said environment of an animal can include, but is not limited to, bedding, furniture, dwellings, vehicles and plants.

DETAILED DESCRIPTION OF THE INVENTION

Figure 1:
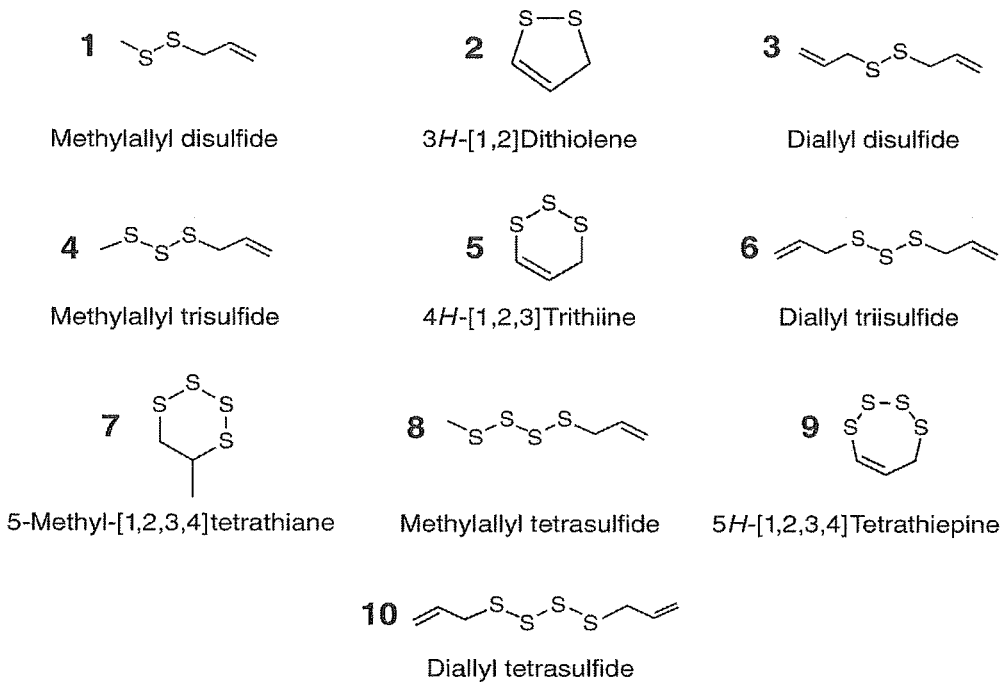
FIG. 1 illustrates flame ionization detector (FID) and electroantennograhic detector (EAD: male or female *Aedes aegypti* antennae) responses to aliquots of the low boiling temperature portion of garlic oil extract. Chromatography: Hewlett Packard (HP) gas chromatograph equipped with a fused silica column (30 m×0.32 mm ID) coated with DB-5; injector and detector temperature: 250° C.; temperature program: 50° C. (held for 1 min, 10° C. per min to 160° C., then 20° C. per min to 300° C. The molecular structure and name of Compounds 1-10 that elicited responses from antennae are depicted above the GC-EAD trace. Antennal stimulatory components 11, 12, 13 and 14 (see TABLE 2) elute later than 13.5 min in the gas chromatogram. Trace components 11-14 are detectable by FID and EAD particularly after heating garlic oil in open Petri dishes at 40° C. for 12 hours, thus enhancing their absolute and relative abundance.
Figure 1:
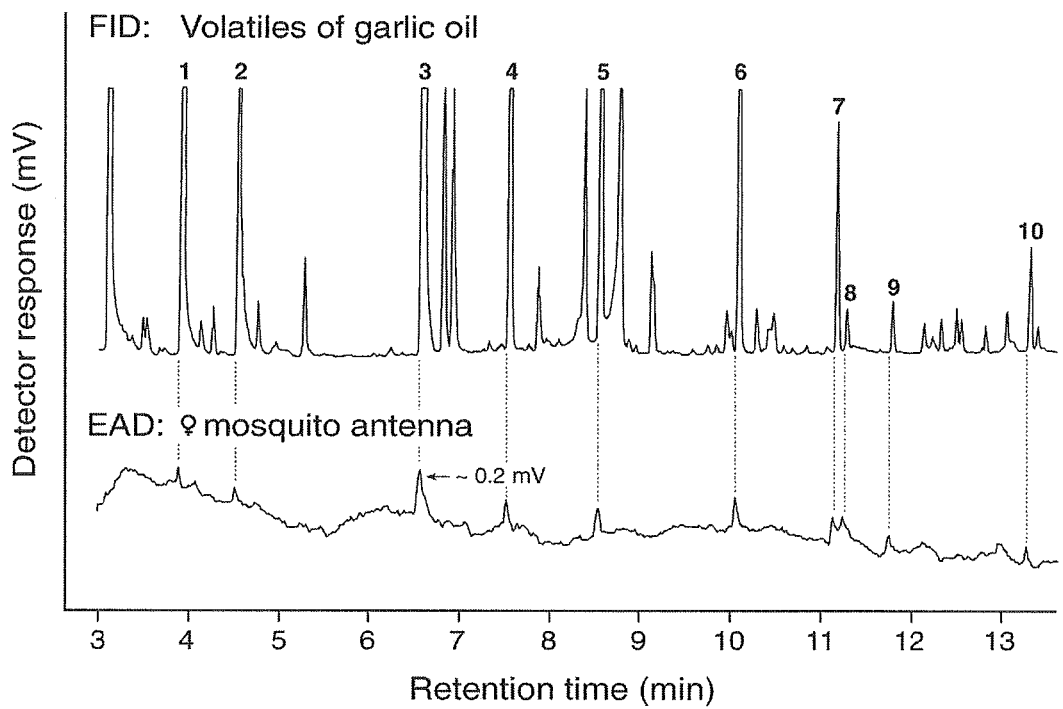

Past research and practice has demonstrated that garlic, *Allium sativum*, and preparations therefrom, can be repellent to mosquitoes and other blood-feeding ectoparasitic arthropods. One study claims that allyl sulfide in combination with Vitamin $B_1$ causes repellence of fleas when ingested by dogs, but neither Vitamin $B_1$ nor garlic oil (erroneously assumed to be composed solely of allyl sulfide) was effective alone, and repellence caused directly by the blend was never demonstrated.

In contrast to this prior art, we have discovered unexpectedly that repellence of blood-feeding ectoparasitic arthropods, and deterrence of landing and feeding by such arthropods, is imparted by the presence of one or more allyl sulfide, allyl disulfide or allyl polysulfide moieties in various compounds found in garlic oil. We have further discovered unexpectedly that synthetic molecules not found in garlic oil, but incorporating one or more of these moieties in their molecular structure, can have repellent and deterrent properties in excess of those imparted by compounds that occur naturally in garlic or garlic oil. Of particular interest for repellent and deterrent properties is the family of compounds comprising aliphatic alcohols with an allylsulfide moiety, including the novel compound 8-allylsulfanyloctan-1-ol. In accordance with these discoveries, it is an object of this invention to provide methods and compositions that may be used in protecting animals, including humans, from vectored disease-causing pathogens, and from biting and annoyance caused by mosquitoes and other blood-feeding ectoparasitic arthropods.

EXAMPLE 1

Experimental Insects

The black-eyed Liverpool strain of *Aedes. aegyti* was obtained from Dr. Carl Lowenberger, Simon Fraser University (SFU). Insects were reared under standardized conditions (60-70% relative humidity, 26-28° C., 14 h light: 10 h dark photoperiod) in SFU's insectary. Neonate larvae that hatched in glass dishes of sterilized hypoxic water were transferred to trays of distilled water provisioned with Nutrafin® Basix Staple Food fish diet. Pupae were collected daily and separated by sex, and 15 females and 10 males were placed in a paper cup (7.5 cm diameter, 8.5 cm high) with a mesh lid. Emergent adults were fed a 10% (w/v) sucrose solution via braided cotton dental rolls. Arm-fed gravid females were offered water-containing paper cups, lined with paper-towel as an oviposition substrate.

The Ifakara strain of *Anopheles gambiae* was obtained from Dr. Bernard Roitberg, SFU. Insects were reared under standardized conditions (see above) in SFU's insectary. Neonate larvae that hatched in glass dishes of distilled water were transferred to trays (250-500 larvae/tray) of distilled water, and provisioned with fish diet ad libitum (see above). Pupae were collected and separated daily and placed in a paper cup with a mesh lid (30-45 pupae/cup). Emergent adults were fed a 10% (w/v) sucrose solution via braided cotton dental rolls. Arm-fed gravid females were offered a water-containing dish (9 cm diameter) with moistened filter paper as an oviposition substrate.

*Culex quinquefasciatus* were obtained from Erin Vrzal of the United States Department of Agriculture (USDA), Gainesville, Fla. Insects were reared in SFU's quarantine facility at 40-50% relative humidity, 25-27° C., and a photoperiod of 14 h light and 10 h dark. Neonate larvae that hatched in glass dishes of distilled water were transferred to trays (250-500 larvae/tray) of distilled water, and provisioned with fish diet ad libitum (see above). Pupae were collected and separated daily and placed in a paper cup with a mesh lid (30-45 pupae/cup). Emergent adults were fed a 10% (w/v) sucrose solution via braided cotton dental rolls. Arm-fed gravid females were offered a water-containing dish for oviposition.

EXAMPLE 2

General Bioassay Procedure

Candidate repellents and deterrents were bioassayed according to a modified protocol from the World Health Organization (1996). At least 1 hour prior to each bioassay, 75 host-seeking non blood-fed, nulliparous, 5- to 8-day-old female *Aedes aegypti, Anopheles gambiae* or *Culex quinquefasciatus* were placed into a wood-framed cage (26.5 cm on each side and 42.5 cm high) with a wooden floor, screened mesh sides and top, and a clear acrylic front fitted with a cotton stockinette sleeve (10 cm diameter). The test subject's arm was covered with an elbow-length polyethylene glove with an excised patch (16.6 cm long, 6 cm wide) to expose the ventral forearm of the test subject. Candidate deterrents were formulated in mineral (paraffin) oil and applied to the exposed forearm 5 min prior to inserting the arm into the cage. The inserted arm remained in the cage for 3 min every 30 min. Prior to each 3-min bioassay period, the hand of the untreated arm was inserted into the cage to ascertain that it received 10 bites within 30 sec as an indication of "biting pressure".

The bioassay was terminated when the treated arm received ≥2 bites in one 3-min bioassay period or one bite in each of two consecutive bioassay periods. The time elapsed from experiment initiation to first bite was recorded as deterrent failure or complete protection time. Percentage repellency at the time the deterrent failed to protect the exposed forearm was calculated by the equation $(C-T)/C \times 100$, where C and T represent the numbers of mosquitoes landing on and/or biting the control and treatment arm, respectively (Tawatsin et al. 2001).

N,N-diethyl-m-toluamide formulated in ethanol at a corresponding dose served as a positive control, and mineral oil by itself served as a negative control. On each day, only one candidate compound was tested, ensuring that any residual material in the chamber had disappeared before the next bioassay.

EXAMPLE 3

Repellence and Deterrence of Garlic Oil and Identification of Bioactive Ingredients Garlic oil (*Allium sativum*—Mexico; Clearwater Soap Works, Box 1775 RR1, Clearwater, BC V0E 1N0, Canada) was formulated in mineral oil and tested using the general bioassay procedure described in EXAMPLE 2 at a dose of 0.1 mg per cm$^2$ of arm surface. It expressed repellence and deterrence for ~30 min.

Aliquots of garlic oil extracts were then subjected to coupled gas chromatographic-electroantennographic detection (GC-EAD) analysis. Fourteen components (10 shown in FIG. 1) elicited responses from female or male mosquito antennae. Some of these components were isolated by high-performance liquid chromatography (HPLC) for identification by nuclear magnetic resonance spectroscopy (NMR). Other components were identified (compounds 11-14 in TABLE 2) by coupled GC-mass spectrometry and by retention index calculations. Assignment of molecular structure for an antennal stimulatory constituent was confirmed by comparing its GC retention time and mass spectrum with that of an authentic standard that was purchased or synthesized. Four of the 10 components in FIG. 1 were tentatively identified by comparing their mass spectra and retention indices with those reported in the literature (Block et al. 1998).

Some of the 10 components in FIG. 1 were bioassayed singly (see general bioassay procedure) and in various combinations, all of which were as deterrent to mosquitoes as garlic oil.

Mosquito-Deterrent Fractions of Garlic Oil

To determine the most deterrent component(s) in garlic oil, it was fractionated by HPLC into four fractions, each containing one or more of the EAD-active components (compounds 1-10 in FIG. 1 and 11-14 in TABLE 2). Each fraction was then bioassayed and shown to be similarly effective in repelling and deterring mosquitoes.

Components with high molecular weight (>250 daltons) are advantageous in that they: 1) dissipate slowly from treated surfaces; 2) provide long-lasting protection against mosquitoes and 3) convey little, if any, offensive smell. The relative abundance of such components was enhanced by treating garlic oil under vacuum, thus stripping away lower-boiling components. In GC-EAD analyses of the high-boiling residue, four components elicited responses from mosquito antennae. They were identified as 4,5,9,10-tetrathiatrideca-1,12-diene, 6-methyl-4,5,8,9-tetrathiadodeca-1,11-diene, 2-(2,3-dithia-5-hexenyl)-3,4-dihydro-2(H)-thiopyran and 3-(2,3-dithia-5-hexenyl)-3,4-dihydro-2(H)-thiopyran (Block et al. 1998) (Compounds 11-14 in TABLE 2), and shown to have a strong repellent and deterrent effect in bioassays.

EXAMPLE 4

Relationship Between Molecular Structure and Deterrence

Figure 2:
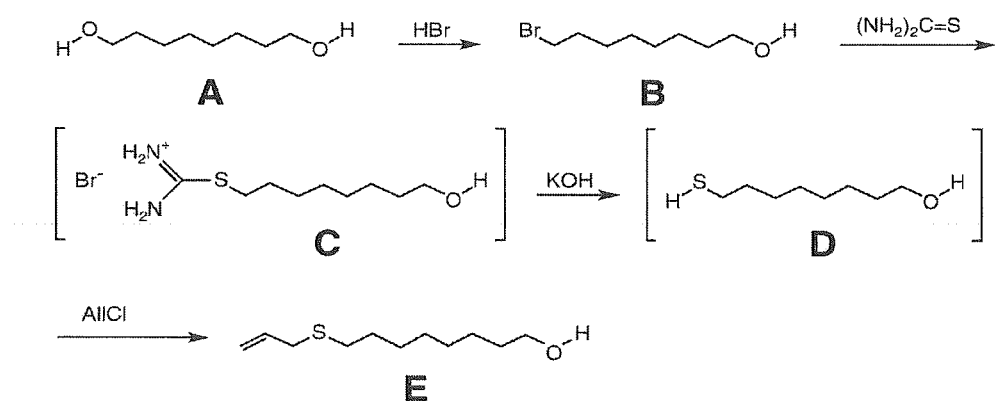
FIG. 2 illustrates a four-step, two-pot synthetic pathway to 8-allylsulfanyloctan-1-ol.

To determine the part of the molecule responsible for deterrence, we synthesized compounds 15-24 (TABLE 2). Synthesis of 8-allylsulfanyloctan-1-ol (Compound 24 in TABLE 2) is described as an example of the preparation of new semiochemical repellents (see FIG. 2).

1,8-Octanediol (A) was purchased from Alfa Aesar and was converted in a 1-step synthesis to 8-bromo-1-octanol (B, 60-70% yield) by continuous liquid-liquid extraction with n-heptane and 48% aqueous hydrobromic acid. By maintaining the aqueous level at ambient temperature, alcohol B was produced with >99% purity. Warming the aqueous layer to 50-55° C. accelerated the reaction by >10 times but increased the by-product 1,8-dibromooctane from 0.6% to 1.8-2.0%. After removal of heptane in vacuo, alcohol B was used as is.

Alcohol B (9.7 g, 46.4 mmol) was stirred with thiourea (4.0 g, 52.6 mmol) in 95% ethanol (150 mL). The mixture was refluxed for 6 h to allow formation of the isothiuronium salt C that was not isolated. To this mixture, 5.6 g of KOH pellets were added in one portion. After another 2.5 h of reflux, the mixture was cooled to room temperature and, without isolating thio-alcohol D or its potassium salt, 6 ml of allyl chloride (73 mmol) were added in one portion. After stirring the reaction mixture overnight, water (150 mL) and a 1:1 mixture of ether/hexane (200 mL) were added. Products were extracted, and the organic phase was washed with water and brine, and dried (anh. MgSO$_4$). Solvents were removed in vacuo, and the crude reaction mixture was filtered through silica (25 g), using in sequence hexane and a 1:1 mixture of hexane-ether as eluents to remove non-polar impurities, such as diallyldisulfane, and to obtain desired 8-allylsulfanyl-octan-1-ol (E). The yield of E (>99% pure based on gas chromatography) was 8.1 g (40.0 mmol, 86.2%). The following mass spectrometric fragmentation ions [m/z (relative abundance)] of E were obtained: 203 (M+1, 28), 202 (M, 53), 143 (50), 142 (17), 131 (53), 101 (23), 87 (100), 85 (26), 81 (24), 79 (15), 74 (66), 73 (23), 69 (32), 68 (17), 67 (73), 59 (28), 55 (51), 53 (15), 47 (15), 45 (48), 41 (91). Nuclear magnetic resonance (NMR) data were as follows: $^1$H NMR (600 MHz, CD$_3$CN): δ 1.20-1.40 (m, 8H), 1.45 (m, 2H), 1.53 (m, 2H), 2.43 (m, 2H), 3.11 (dt, J=7.2, 0.9 Hz, 2H), 3.46 (dt, J=6.6, 5.4 Hz, 2H), 5.05 (tdd, J=10.0, 1.8, 0.9 Hz, 1H) 5.08 (m, 1H), 5.78 (tdd, J=17.0, 10.0, 7.2 Hz, 1H). $^{13}$C NMR (CD$_3$CN): δ 26.9, 29.8, 30.2, 30.3, 30.4, 31.4, 33.9, 35.2, 62.8, 117.3, 136.4.

In bioassays, neither compound 20 (the sulfur atoms replaced by an oxygen atoms) nor compound 21 (containing no hetero atoms) had any repellence or deterrence. Furthermore, taking other results in TABLE 2 and in FIG. 1 into account, there is compelling evidence that repellence and deterrence is expressed by molecules with one or more allyl sulfide, allyl disulfide, or allyl polysulfide moieties. Further repellence and deterrence can be obtained by combining in the same compound one or more allyl sulfide, allyl disulfide or allyl polysilfide moieties with one or more hydroxyl moieties.

A compound with commercial appeal should be 1) odorless, 2) stable, 3) easy and inexpensive to synthesize, 4) non-toxic, and 5) deterrent for a long time. Compound 24 (TABLE 2) appears to meet all these requirements. It has almost no detectable odor and it is very potent, even at a low dose.

TABLE 2

Failure time and percent repellency in experiments with *Aedes aegypti* testing garlic oil semiochemicals 11-14, synthetic analogues (Compounds 15-24), and N,N-diethyl-m-toluamide (DEET) (Compound 25).

| Substance[a] | | Dosage mg/cm$^2$ | Failure time (min)[b] | Percent repellence[c] |
|---|---|---|---|---|
| 11 | [structure] | 0.1<br>>0.1 | 0<br>67.7 | 85<br>92 |
| 12 | [structure] | 0.1<br>0.5 | 0<br>102 | 87<br>97 |
| 13, 14 | [structures] | 0.1 | 35 | 93 |

TABLE 2-continued

Failure time and percent repellency in experiments with *Aedes aegypti* testing garlic oil semiochemicals 11-14, synthetic analogues (Compounds 15-24), and N,N-diethyl-m-toluamide (DEET) (Compound 25).

| Substance[a] | Dosage mg/cm$^2$ | Failure time (min)[b] | Percent repellence[c] |
|---|---|---|---|
| 15 | 0.1 | 34 | 92 |
| 16 | 0.1 | 35 | 89 |
|  | 0.5 | 36 | 92 |
| 17 | 0.1 | 0 | 89 |
|  | 0.5 | 36 | 97 |
| 18 | 0.5 | 67 | 93 |
| 19 | 0.1 | 0 | 93 |
|  | 0.5 | 102 | 97 |
| 20 | 0.1 | 0 | 81 |
| 21 | 0.1 | 0 | 50 |
| 22 | 0.05 | 33 | — |
| 23 | 0.05 | 99 | — |
| 24[d] |  |  |  |
| 25[e] DEET |  |  |  |

[a]Compound names as follows: 11 = 4,5,9,10-tetrathiatrideca-1,12-diene; 12 = 6-methyl-4,5,8,9-tetrathiadodeca-1,11-diene; 13 = 2-(2,3-dithia-5-hexenyl)-3,4-dihydro-2(H)-thiopyran; 14 = 3-(2,3-dithia-5-hexenyl)-3,4-dihydro-2(H)-thiopyran; 15 = 1,2-bis-(1,2-dithia-4-pentenyl)-benzene; 16 = (E)-4,5-dithia-1,7-octadien-1-yl-benzene; 17 = 4,8-dithiaundeca-1,10-diene; 18 = 4,11-dithiatetradeca-1,13-diene; 19 = 4,13-dithiahexadeca-1,15-diene; 20 = 1,10-bis-allyloxy-decane; 21 = octadeca-1,17-diene: 22 = 9-allylsulfanylnonan-1-ol; 23 = 8-allylsulfanyloctan-2-ol; 24 = 8-allylsulfanyloctan-1-ol.

[b]A failure time of zero indicates immediate failure (i.e. biting occurred), even though the percent repellence may be high.

[c]See EXAMPLE 2 for method of calculating percent repellence.

[d]For bioassay result see EXAMPLES 5-7

[e]For bioassay result see EXAMPLE 8

EXAMPLE 5

Repellence and Deterrence of 8-allylsulfanyloctan-1-ol Against *Aedes aegypti*

To determine the repellence and deterrence of 8-allylsulfanyloctan-1-ol against *Aedes aegypti*, a 5%, 10% or 25% formulation of 8-allylsulfanyloctan-1-ol in mineral oil was applied in Experiments 1-3 at a dose of 1.5 mg (total composition) per $cm^2$ to the skin of the test person, and was bioassayed according to the protocol described under EXAMPLE 2. In Experiment 4, mineral oil by itself served as a negative control and was bioassayed at the same dose (1.5 mg per $cm^2$) as in Experiments 1-3. Each of Experiments 1-4 was replicated four times.

Figure 3:
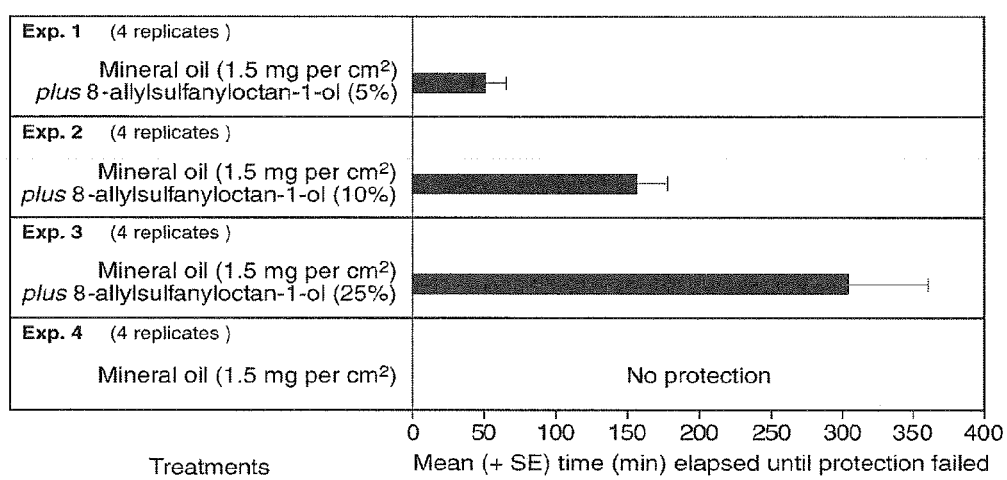
FIG. 3 shows the duration of protection of a 100 $cm^2$ area of an exposed human forearm from bites by *Aedes aegypti* caused by 5%, 10% and 25% formulations of 8-allylsulfanyloctan-1-ol in mineral oil applied to the skin at a dose of 1.5 mg per $cm^2$, as opposed to no protection provided by mineral oil alone.

In Experiments 1, 2 and 3, 5%, 10% and 25% formulations of 8-allylsulfanyl-octan-1-ol in mineral oil provided protection from bites by *Aedes egypti* on average for 52 min, 157 min and 305 min, respectively (FIG. 3). In Experiment 4, mineral oil by itself failed to provide any protection from bites (FIG. 3).

EXAMPLE 6

Repellence and Deterrence of 8-allylsulfanyloctan-1-ol Against *Anopheles gambiae*

To determine the repellence and deterrence of 8-allylsulfanyloctan-1-ol against *Anopheles gambiae*, a 2%, 5% or a 10% formulation of 8-allylsulfanyloctan-1-ol in mineral oil was applied in Experiments 5-7 at a dose of 1.5 mg per $cm^2$ to the skin of the test person, and was bioassayed according to the protocol described under EXAMPLE 2. In Experiment 8, mineral oil by itself served as a negative control and was tested at the same dose (1.5 mg per $cm^2$) as in Experiments 5-7. Each of Experiments 5-8 was replicated 4 times.

Figure 4:
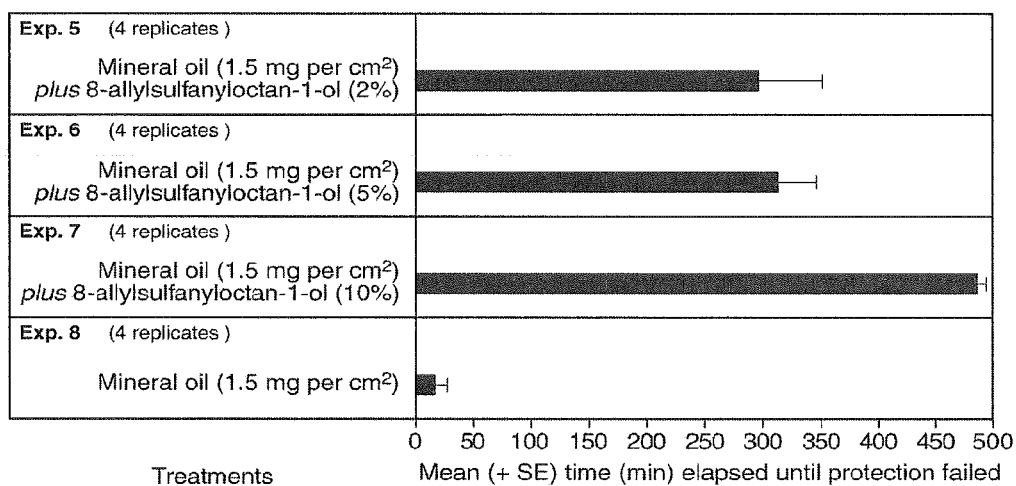
FIG. 4 shows the duration of protection of a 100 $cm^2$ area of an exposed human forearm from bites by *Anopheles gambiae* caused by 5% and 10% formulations of 8-allylsulfanyloctan-1-ol in mineral oil applied to the skin at a dose of 1.5 mg per $cm^2$, as opposed to negligible protection provided by mineral oil alone.

In Experiments 5, 6 and 7, 2%, 5% and 10% formulations of 8-allylsulfanyloctan-1-ol in mineral oil provided protection from bites by *Anopheles gambiae* on average for 297 min, 314 min and 487 min, respectively (FIG. 4). In Experiment 8, mineral oil by itself failed to provide appreciable protection (FIG. 4).

EXAMPLE 7

Repellence and Deterrence of 8-allylsulfanyloctan-1-ol Against *Culex quinquefasciatus*

To determine the repellence and deterrence of 8-allylsulfanyloctan-1-ol against *Culex quinquefasciatus*, a 2% and 5% or a 10% formulation of 8-allylsulfanyloctan-1-ol in mineral oil was applied in Experiments 9-11 at a dose of 1.5 mg per $cm^2$ to the skin of the test person, and was bioassayed according to the protocol described under EXAMPLE 2. In Experiment 12, mineral oil by itself served as a negative control and was tested at the same dose (1.5 mg per $cm^2$) as in Experiments 9 and 10. Each of Experiments 9-11 was replicated 4 times.

Figure 5:
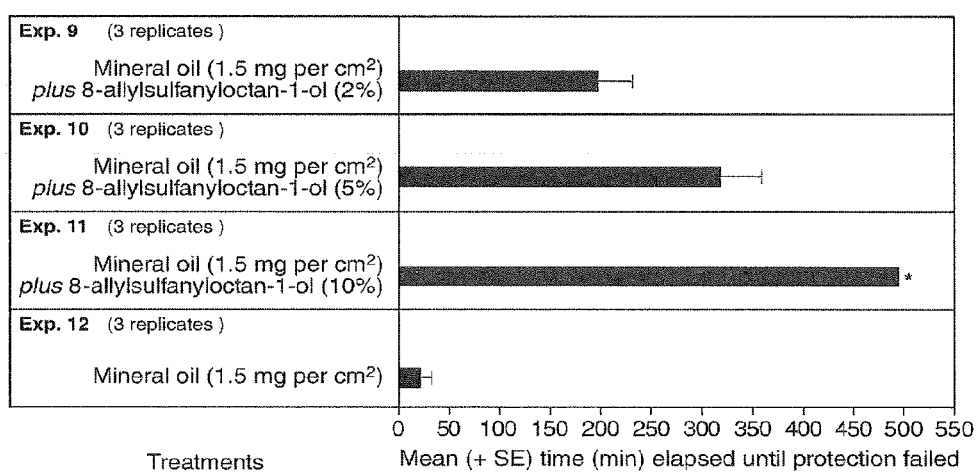
FIG. 5 shows the duration of protection of a 100 $cm^2$ area of an exposed human forearm from bites by *Culex quinquefasciatus* caused by 2% and 10% formulations of 8-allylsulfanyloctan-1-ol in mineral oil applied to the skin at a dose of 1.5 mg per $cm^2$, as opposed to negligible protection provided by mineral oil alone.* In each of the three replicates in Experiment 11, there was complete protection against bites when the experiment was terminated after eight hours.

In Experiments 9, 10 and 11, 2%, 5% and 10% formulations of 8-allylsulfanyloctan-1-ol in mineral oil provided protection from bites by *Culex quinquefasciatus* on average for 198 min, 319 min, and 495 min, respectively (FIG. 5). In each of the three replicates in Experiment 11, there was complete protection against bites when the experiment was terminated after eight hours. Thus, the protection time is even greater than illustrated conservatively in FIG. 5. In Experiment 12, mineral oil by itself failed to provide appreciable protection (FIG. 5).

EXAMPLE 8

Comparison of Repellence and Deterrence Caused by N,N-Diethyl-m-toluamide and by 8-allylsulfanyloctan-1-ol Against *Anopheles gambiae*

To be able to compare the repellence and deterrence caused N,N-diethyl-m-toluamide (DEET), and by 8-allylsulfanyloctan-1-ol, Experiment 13 tested a 2% formulation of N,N-diethyl-m-toluamide in ethanol (the best formulant for this compound) for protection from bites by *Anopheles gambiae*. A dose of 1.5 mg per $cm^2$ was applied to the skin of the test person and bioassayed according to the protocol described under EXAMPLE 2.

Figure 6:
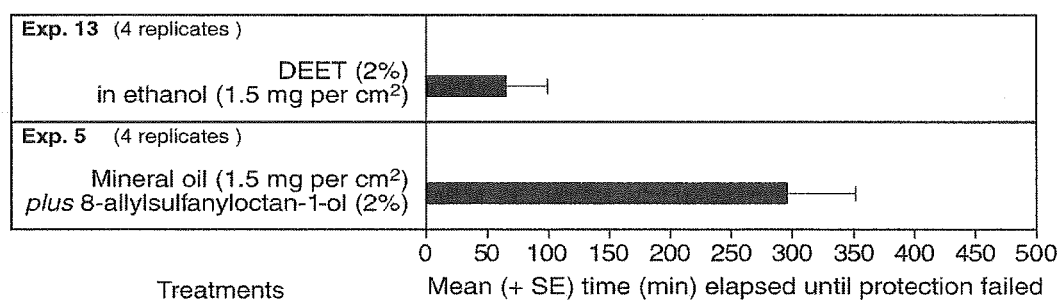
FIG. 6 shows the duration of protection of a 100 $cm^2$ area of an exposed human forearm from bites by *Anopheles gambiae* caused by a 2% formulation of 8-allylsulfanyloctan-1-ol in mineral oil applied at a dose of 1.5 mg per $cm^2$, compared to the duration of protection caused by a 2% formulation of N,N-diethyl-m-toluamide (DEET) applied at the same dose.

In Experiment 13, a 2% formulation of N,N-diethyl-m-toluamide provided protection from bites by *Anopheles gambiae* on average for 66 min (FIG. 6). Unexpectedly, and in contrast, the duration of protection provided by N,N-diethyl-m-toluamide was only one sixth of the 297 min protection provided by a 2% formulation of 8-allylsulfanyl-octan-1-ol in Experiment 5 (FIG. 6; see also FIG. 4).

EXAMPLE 9

Formulation of Emulsion No. 1

The components, amounts and proportions of Emulsion No. 1 were: distilled water 0.35 g, 23%; light paraffin oil (EMD Chemicals) 0.53 g, 35%; glycerol (Anachemia) 0.27 g, 18%; soy lecithin (Xenex Labs) 0.21 g, 14%; 8-allylsulfanyloctan-1-ol 2.0-6.7% (if added); ethanol 0.05 mL (quickly evaporating and not remaining as part of the emulsion); vanillin (BDH Laboratory Chemicals) 2.0-6.7% (if added). According to amounts of the active ingredients 8-allylsulfanyloctan-1-ol and vanillin, the percentage of other constituents was slightly adjusted accordingly.

A vessel was charged with water, glycerol, paraffin oil, soy lecithin, and 8-allylsulfanyl-octan-1-ol (if added) in the above order and mixed to homogeneity after each addition. If vanillin was added, a second vessel was charged with ethanol and vanillin, stirring the mixture until vanillin was completely dissolved; the vanillin solution was then added to the first vessel and vortexed for several minutes to achieve homogeneity. If vanillin was not added, ethanol was added to the first vessel and vortexed for several minutes to achieve homogeneity.

EXAMPLE 10

Formulation of Emulsion No. 2

The components, amounts and proportions of Emulsion No. 2 were: Structure ZEA (hydroxypropyl cellulose) (National Starch and Chemical Co.) 0.16 g, 4%; distilled water 2.56 g, 63%; glycerol (Sigma-Aldrich) 0.21 g, 5%; Stepanquat ML [methyl sulfate quaternary ammonium salt of the esterification of oleic acid with N,N,N',N'-tetrakis(2-hydroxypropyl) ethylene-diamine] (Stepan Co.) 0.12 g, 3%; isopropanol (Anachemia) 0.21 g, 5%; Lipocol L (Lipo Chemicals Inc.) 0.06 g, 2%; 8-allylsulfanyloctan-1-ol 0.41 g, 10%; and vanillin (Sigma-Aldrich) 0.32 g, 8%.

Structure ZEA was charged into a vessel, water was added, and the components were mixed to homogeneity. A second vessel was charged with the glycerol, the Stepanquat ML, the isopropanol, the Lipocol L, 8-allylsulfanyloctan-1-ol, and vanillin in the above order. After each addition, the resulting mixture was stirred for several minutes. The water/Structure ZEA homogenate was then added slowly to the rapidly mixing organic mixture over several minutes. After mixing was completed, the gross emulsion was homogenized @ 30,000 rpm for several minutes.

EXAMPLE 11

Test of Emulsion No. 1 Compositions with 8-allylsulfanyloctan-1-ol and Vanillin Against *Aedes aegypti*

To compare the repellence and deterrence against *Aedes aegypti* caused by 8-allylsulfanyloctan-1-ol as a single active ingredient and by 8-allylsulfanyloctan-1-ol in combination with vanillin as a second active ingredient, we tested a 6.7% emulsion of vanillin (Experiment 14), a 6.7% emulsion of 8-allylsulfanyloctan-1-ol (Experiment 15), and a 13.4% emulsion of 8-allylsulfanyloctan-1-ol plus vanillin (1:1 ratio) (Experiment 16). 8-Allylsulfanyloctan-1-ol and vanillin were formulated in Emulsion No. 1 (see EXAMPLE 9). In each of Experiments 13-15, test stimuli were applied at a dose of 1.5 mg per cm$^2$ to the skin of the test person, and were bioassayed according to the protocol described under EXAMPLE 2. In Experiment 17, Emulsion No. 1 served as a positive control and was tested at the same dose (1.5 mg per cm$^2$) as in Experiments 14-16.

Figure 7:
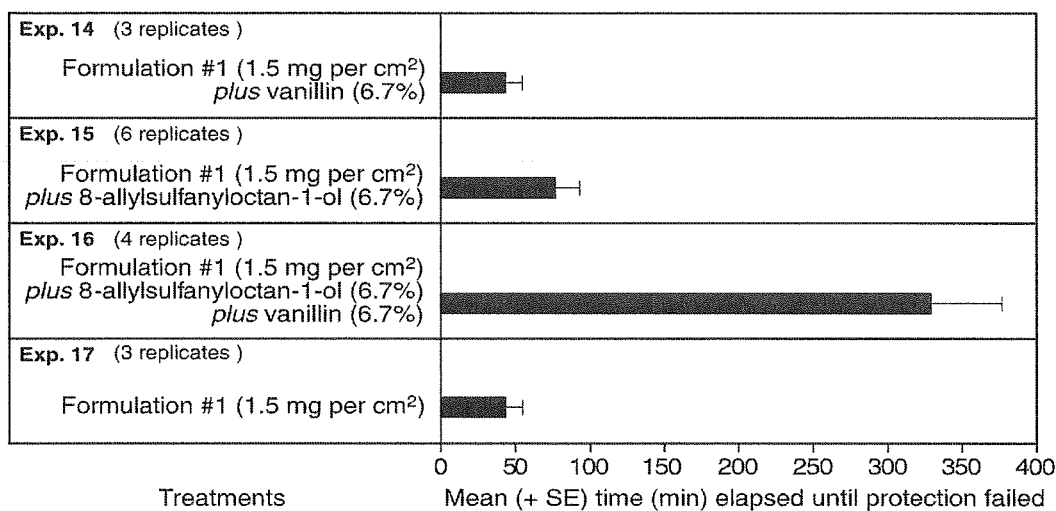
FIG. 7 shows the duration of protection of a 100 $cm^2$ area of an exposed human forearm from bites by *Aedes aegypti* caused by a composition of 8-allylsulfanyloctan-1-ol (6.7%) in Emulsion No. 1, vanillin (6.7%) in Emulsion No. 1, both vanillin (6.7%) and 8-allylsulfanyloctan-1-ol (6.7%) in Emulsion No. 1, and by Emulsion No. 1 alone. All compositions applied to the skin at 1.5 mg per $cm^2$.

In Experiments 14, 15 and 16, vanillin, 8-allylsulfanyloctan-1-ol, and 8-allylsulfanyl-octan-1-ol plus vanillin provided protection from bites by *Aedes aegypti* on average for 44 min, 77 min and 330 min, respectively (FIG. 7). These results indicate that there is an unexpected synergistic interaction between 8-allylsulfanyloctan-1-ol and vanillin. In Experiment 17, Emulsion No. 1 composition by itself failed to provide any protection (FIG. 7).

EXAMPLE 12

Test of Emulsion No. 1 Compositions with 8-allylsulfanyloctan-1-ol and Vanillin Against *Anopheles gambiae*

To compare the repellence and deterrence against *Anopheles gambiae* caused by 8-allyl-sulfanyloctan-1-ol as a single active ingredient and by 8-allylsulfanyloctan-1-ol in combination with vanillin as a second active ingredient, we tested a 6.7% emulsion of vanillin (Experiment 18), a 6.7-% emulsion of 8-allylsulfanyl-octan-1-ol (Experiment 19) and a 13.4% emulsion of 8-allylsulfanyloctan-1-ol plus vanillin (1:1 ratio) (Experiment 20). 8-Allylsulfanyloctan-1-ol and vanillin were formulated in Emulsion No. 1 (see EXAMPLE 9). In each of Experiments 18-20, test stimuli were applied at a dose of 1.5 mg per cm$^2$ to the skin of the test person, and were bioassayed according to the protocol described under EXAMPLE 2. In Experiment 21, Emulsion No. 1 served as a positive control and was tested at the same dose (1.5 mg per cm$^2$) as in experiments 18-20. Each of Experiments 18-21 was replicated three times.

Figure 8:
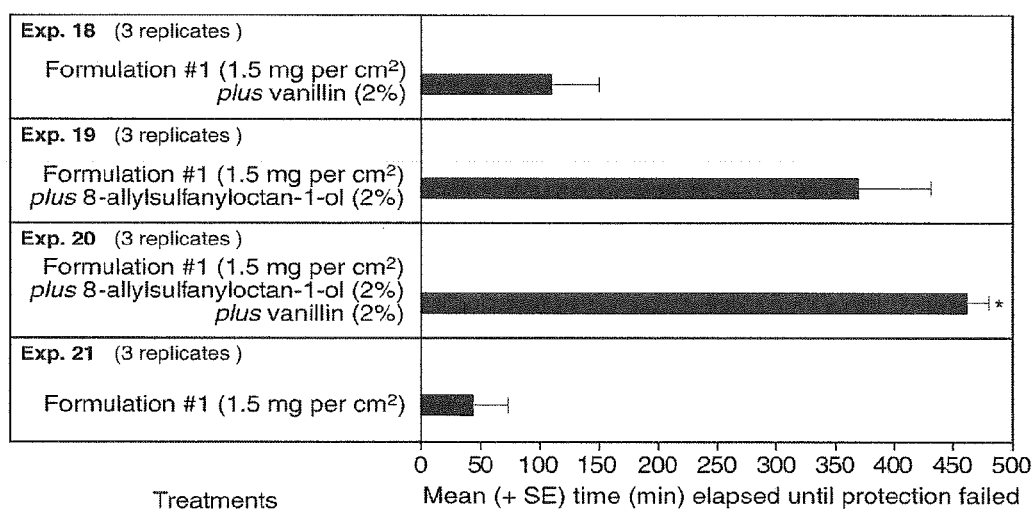
FIG. 8 shows the duration of protection of a 100 $cm^2$ area of an exposed human forearm from bites by *Anopheles gambiae* caused by a composition of 8-allylsulfanyl-octan-1-ol (2.0%) in Emulsion No. 1, vanillin (2.0%) in Emulsion No. 1, both vanillin (2.0%) and 8-allylsulfanyloctan-1-ol (2.0%) in Emulsion No. 1, and by Emulsion No. 1 alone. All compositions applied to the skin at 1.5 mg per $cm^2$.* In two of the three replicates in Experiment 20, there was complete protection against bites when the experiment was terminated after eight hours.

In Experiments 18-21, vanillin, 8-allylsulfanyloctan-1-ol and 8-allylsulfanyloctan-1-ol plus vanillin provided protection from bites by *Anopheles gambiae* on average for 110 min, 369 min and 462 min, respectively (FIG. 8). In two of the three replicates in Experiment 20, there was complete and unexpected protection against bites for eight hours, after which the experiment was terminated. Thus, the protection time is even greater than illustrated conservatively in FIG. 8. The results indicate that there is an interactive effect between 8-allylsulfanyloctan-1-ol and vanillin. In Experiment 21, Emulsion No. 1 by itself failed to provide appreciable protection (FIG. 8).

EXAMPLE 13

Test of Emulsion No. 1 Compositions with 8-allylsulfanyloctan-1-ol and Vanillin Against *Culex quinquefasciatus*

To compare the repellence and deterrence against *Culex quinquefasciatus* caused by 8-allylsulfanyloctan-1-ol as a single active ingredient and by 8-allylsulfanyloctan-1-ol in combination with vanillin as a second active ingredient, we tested a 6.7% emulsion of vanillin (Experiment 22), a 6.7% emulsion of 8-allylsulfanyloctan-1-ol (Experiment 23) and a 13.4% emulsion of 8-allylsulfanyloctan-1-ol plus vanillin (1:1 ratio) (Experiment 24). 8-Allylsulfanyloctan-1-ol and vanillin were formulated in Emulsion No. 1 (see EXAMPLE 9). In each of Experiments 21-24, test stimuli were applied at a dose of 1.5 mg per cm$^2$ to the skin of the test person, and were bioassayed according to the protocol described under EXAMPLE 2. In Experiment 25, Emulsion No. 1 served as a positive control and was tested at the same dose (1.5 mg per cm$^2$) as in Experiments 22-24. Each of Experiments 22-25 was replicated three times.

Figure 9:
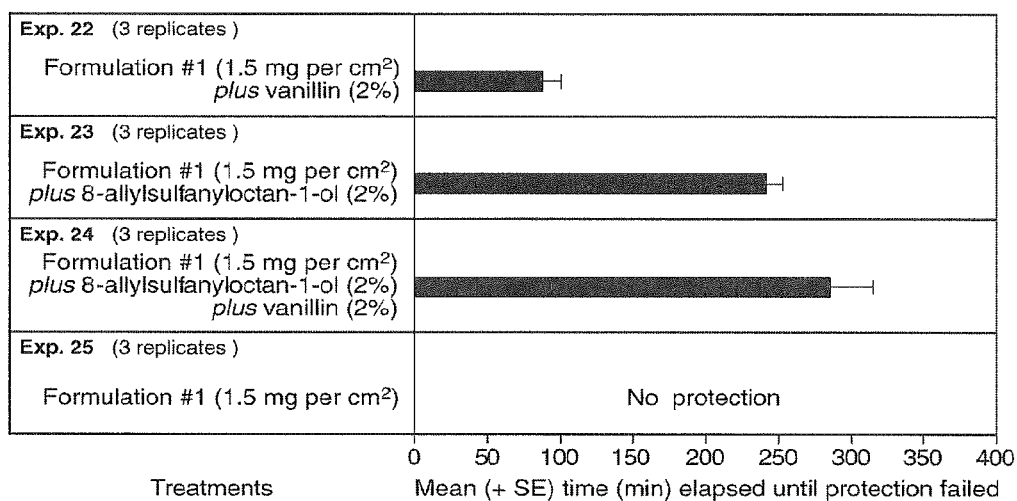
FIG. 9 shows the duration of protection of a 100 $cm^2$ area of an exposed human forearm from bites by *Culex quinquefasciatus* caused by a composition of 8-allylsulfanyl-octan-1-ol (2.0%) in Emulsion No. 1, vanillin (2.0%) in Emulsion No. 1, both vanillin (2.0%) and 8-allylsulfanyloctan-1-ol (2.0%) in Emulsion No. 1, and by Emulsion No. 1 alone. All compositions applied to the skin at 1.5 mg per $cm^2$.

In Experiments 22-24, vanillin, 8-allylsulfanyloctan-1-ol and 8-allylsulfanyloctan-1-ol plus vanillin provided protection from bites by *Culex quinquefasciatus* on average for 88 min, 242 min and 286 min, respectively (FIG. 9). These results indicate that there is an interactive effect between 8-allylsulfanyloctan-1-ol and vanillin. In Experiment 25, Emulsion No. 1 by itself failed to provide any protection (FIG. 9).

EXAMPLE 14

Comparison of Deterrence Against *Aedes aegypti* Caused by N,N-diethyl-m-toluamide in Ethanol and by 8-allylsulfanyloctan-1-ol Plus Vanillin in Compositions Formulated in Emulsions No. 1 or No. 2

To be able to compare the repellence and deterrence caused by N,N-diethyl-m-toluamide and by 8-allylsulfanyloctan-1-ol plus vanillin in Emulsion No. 1 (EXAMPLE 9), Experiment 26 tested a 6.7% formulation of N,N-diethyl-m-toluamide in ethanol (the best formulant for DEET) for protection from bites by *Aedes egypti*. In each replicate, a dose of 1.5 mg per cm was applied to the skin of the test person and bioassayed according to the protocol described under EXAMPLE 2.

Figure 10:
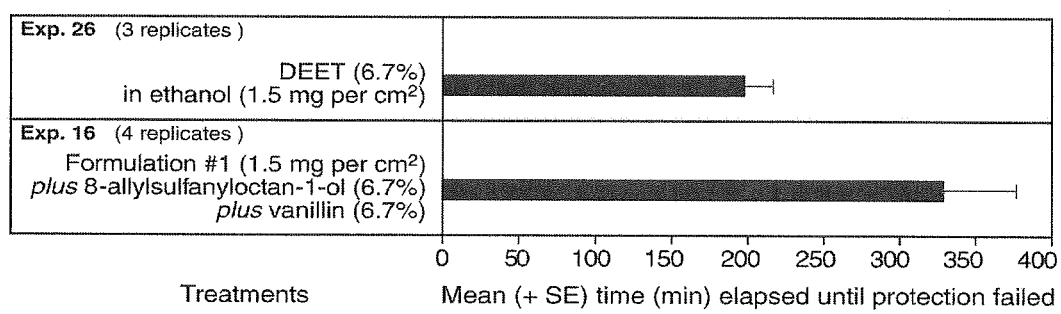
FIG. 10 shows the duration of protection of a 100 $cm^2$ area of an exposed human forearm from bites by *Aedes aegypti* caused by a formulation of N,N-diethyl-m-toluamide (DEET)(6.7%) in ethanol in comparison to a composition of Emulsion No. 1 with vanillin (6.7%) and 8-allylsulfanyloctan-1-ol (6.7%). Both formulations applied to the skin at 1.5 mg per $cm^2$.

In Experiment 26, N,N-diethyl-m-toluamide provided protection from bites by *Aedes aegypti* on average for 197 min (FIG. 10). 8-Allylsulfanyloctan-1-ol (6.7%) plus vanillin (6.7%) in Emulsion No. 1 provided protection on average for 333 min (FIG. 10).

To be able to further compare the deterrence caused by N,N-diethyl-m-toluamide with that caused by 8-allylsulfanyloctan-1-ol plus vanillin, Experiment 27 tested a 10.4% formulation of N,N-diethyl-m-toluamide in ethanol, and Experiment 28 tested 8-allylsulfanyloctan-1-ol (10.4%) plus vanillin (7.9%) in Emulsion No. 2 (EXAMPLE 10). In each replicate of both experiments, a dose of 1.5 mg per cm was applied to the skin of the test person and bioassayed according to the protocol described under EXAMPLE 2.

Figure 11:
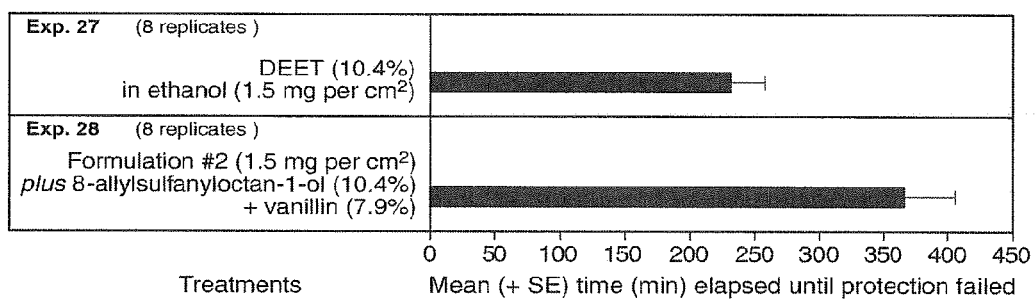
FIG. 11 shows the duration of protection of a 100 $cm^2$ area of an exposed human forearm from bites by *Aedes aegypti* caused by a formulation of N,N-diethyl-m-toluamide (DEET) (10.4%) in ethanol in comparison to a composition of Emulsion No. 2 with vanillin (7.9%) and 8-allylsulfanyloctan-1-ol (10.4%). Both compositions applied to the skin at 1.5 mg per $cm^2$.

In Experiment 28, allylsulfanyloctan-1-ol plus vanillin in Emulsion No. 2 provided protection from bites by *Aedes aegypti* on average for 333 min, considerably longer than the 231 min on average provided by N,N-diethyl-m-toluamide in Experiment 27 (FIG. 11).

As will be apparent to those skilled in the art in the light of the foregoing disclosure, many alterations and modifications are possible in the practice of this invention without departing from the spirit or scope thereof. Accordingly, the scope of the invention is to be construed in accordance with the substance defined by the following claims.

REFERENCES

U.S. Patent Documents

Anderson, W. A. and Brock, B. E. 1998. Mosquito repelling technique. U.S. Pat. No. 5,733,552.
Arand, A. and Arand, J. K. 2002. Garlic composition for foliar applications. U.S. Pat. No. 6,488,950.
Arand, A. and Arand, J. K. 2003. Garlic composition for foliar applications. U.S. Pat. No. 6,511,674.
Bassett, J. M. 1998. Insect repellent. U.S. Pat. No. 5,711,953.
Beldock, D. T., Beldock, J. A., and Mudge, G. 1997. Insect repellent blends, lotions and sprays. U.S. Pat. No. 5,621,013.
Butler, J. F. 2001. Method for inhibiting from feeding, cockroaches. U.S. Pat. No. 6,255,356.
Cantrell, C. L., Klun, J. A., and Duke, S. O. 2006. Novel chlerodanes and methods for repelling arthropods. U.S. Patent Application Publication No. US 2006/0235071.
Fried, H. L., Khazan, D., and Morales, M. N. 2007. Environmentally safe insect repellent composition. U.S. Pat. No. 7,201,926.
Hallahan, D. L. 2007. Insect repellent compounds. U.S. Pat. No. 7,232,844.
Hautmann, H. 1979. Insect repellent. U.S. Pat. No. 4,164,561.
Ishiwateri, T. 1999. Arthropod repellent and method for repelling arthropods. U.S. Pat. No. 5,925,371.
McKenzie, J. 1995. Insect repellent for fruits, vegetables and plants. U.S. Pat. No. 5,429,817.
Nichols, L. D. 1993. Insect repellent compositions. U.S. Pat. No. 5,206,022.
Pijoan, M. and Jachowski, L. A., Jr. 1950. Insect repellent mixtures comprising a hydrogenated diphenyl and a hydrogenated naphthol. U.S. Pat. No. 2,512,675.
Polefka, T. G., Ramachandran, P., Steltenkamp, R. J., Connors, T. F., and Kinscherf, K. M. 1997. Insect repelling compositions comprising mixtures of an N-alkyl neoalkanamide and deet. U.S. Pat. No. 5,610,194.
Retnakaran, A. 1984. Repellent for black fly. U.S. Pat. No. 4,427,700.
Roe, R. M. 2002. Method of repelling insects. U.S. Pat. No. 6,437,001.
Roe, R. M. 2004. Method of repelling insects. U.S. Pat. No. 6,800,662.
Roe, R. M. 2007. Method of repelling insects. U.S. Pat. No. 7,288,573.
Ross, J. S. 2003. Insect repellent emulsions. U.S. Pat. No. 6,605,643.
Sherwood, K. and Sherwood, F. 1992. Repellent composition containing natural oils of citronella, cedar and wintergreen and use thereof. U.S. Pat. No. 5,106,622.
Sikinami, Y., Hata, K., and Yasuhara, M. 1991. Controlled release insect pest repellent. U.S. Pat. No. 5,017,377.
Weisler, R. 1989. Systemic insect repellent composition and method. U.S. Pat. No. 4,876,090.
Zhu, B. C. R., Henderson, G., and Laine, R. A. 2005. Dihydronootkatone and tetrahydronootkatone as repellents to arthropods. U.S. Pat. No. 6,897,244.

Publications

Badolo, A., Ilboudo-Sanogo, E., Ouédraogo, A. P., and Costanti, C. 2004. Evaluation of the sensitivity of *Aedes aegypti* and *Anopheles gambiae* complex mosquitoes to two insect repellents: DEET and KBR 3023. *Trop. Med. Int. Hlth.* 9: 330-334.
Barnard, D. R. and Xue, R.-D. 2004. Laboratory evaluation of mosquito repellents against *Aedes albopictus*, *Culex nigripalpus*, and *Ochlerotatus triseriatus* (Diptera: Culicidae). *J. Med. Entomol.* 41: 726-730.
Bhuyan, M., Saxena, N., and Rao, K. M. 1974. Repellent property of oil fraction of garlic, *Allium sativum* (Linn.). *Indian J. Exp. Biol.* 12: 575-576.
Block, E. 1992. The organosulfur chemistry of the genus *Allium*—implications for the organic chemistry of sulfur. *Angew. Chem. Int. Ed. Engl.* 31: 1135-1178.
Block, E., Rajeshwari, I., Grisoni, S., Saha, C., Belman, S., and Lossing, F. P. 1988. Lipoxygenase inhibitors from essential oil of garlic. Markovnikov addition of the allyldithio radical to olefins. *J. Am. Chem. Soc.* 110: 7813-7827.
Cantrell, C. L., Klun, J. A., Bryson, C. T., Kobaisy, M., and Duke, S. O. 2005. Isolation and identification of mosquito bite deterrent terpenoids from leaves of American (*Callicarpa Americana*) and Japanese (*Callicarpa japonica*) beautyberry. *J. Agric. Food Chem.* 53: 5948-5953.
Carroll, J. F., Cantrell, C. L., Klun, J. A., and Kramer, M. 2007. Repellency of two terpenoid compounds isolated from *Callicarpa Americana* (Lamiaceae) against *Ixodes scapularis* and *Amblyomma americanum* ticks. *Exp. Appl. Acarol.* 41: 215-224.
Carroll, S. P., and Loye, J. 2006. PMD, a registered botanical mosquito repellent with DEET-like efficacy. *J. Am. Mosq. Cont. Assoc.* 22: 707-514.
Choochote, W., Chaithong, U., Kamsuk, K., Jitpakdi, A., Tippawangkosol, P., Tuetun, B., Champakaew, D., and Pitasawat, B. 2007. Repellent activity of selected essential oils against *Aedes aegypti*. *Fitoterapia* 78: 359-364.
Fradin, M. S., and Day, J. F. 2002. Comparative efficacy of insect repellents against mosquito bites. *N. Engl. J. Med.* 347: 13-18.
Harwood, R. F. and James, M. T. 1979. Entomology in human and animal health. 7th Ed. Macmillan, New York. 548 pp.
Hill, C. A., Kafatos, F. C., Stansfield, S. K., and Collins, F. H. 2005. Arthropod-borne diseases: vector control in the genomics era. *Nature Rev. Microbiol.* 3: 262-268.
Mackenzie, J. S., Gubler, D. J., and Petersen, L. R. 2004. Emerging flaviviruses: the spread and resurgence of Japanese encephalitis, West Nile and Dengue viruses. *Nature Medicine* 10: S98-S109.
Mairuhu, A. T. A., Wagenaar, J., Brandjes, D. P. M., and van Gorp, E. C. M. 2004. Dengue: and arthropod-borne disease of global importance. *Eur. J. Clin. Microbiol. Infect. Dis.* 23: 425-433.
Malavige, G. N., Fernando, S., Fernando, D. J., and Seneviratne, S. L. 2004. Dengue viral infections. *Postgrad. Med. J.* 80: 588-601.
Miot, H. A., Batistella, R. F., Batista, K. A., Volpato, D. E. C., Augusto, L. S. T., Madeira, N. G., Haddad Jr., V., and Miot, L. D. B. 2004. Comparative study of the topical effectiveness of the andiroba oil (*Carapa guianensis*) and DEET 50% as a repellent for *Aedes* sp. *Rev. Inst. Med. Trop. S. Paulo.* 46: 253-256.

Pest Management Regulatory Agency, Health Canada. 2002. Personal insect repellents containing DEET (N,N-diethyl-m-toluamide and related compounds). Re-evaluation Decision Document No. RRD2002-01. 41 pp.

Miot, H. A., Batistella, R. F., Batista, K. A., Volpato, D. E. C., Augusto, L. S. T., Madeira, N. G., Haddad Jr., V., and Miot, L. D. B. 2004. Comparative study of the topical effectiveness of the andiroba oil (*Carapa guianensis*) and DEET 50% as a repellent for *Aedes* sp. *Rev. Inst. Med. Trop. S. Paulo.* 46: 253-256.

Moore, S. J., Lenglet, A., and Hill, N. 2006. Plant based insect repellents. In: Insect repellents: principles, methods, and uses. CRC Press, Boca Raton, Fla. 495 pp.

Rajan, T. V., Hein, M., Porte, P., Wikel, S. 2005. A double-blinded, placebo-controlled trial of garlic as a mosquito repellant: a preliminary study. *Med. Vet. Entomol.* 19:84-89.

Roe, R. M., Donohue, K. V., and Jones, A. 2006. Development of a novel all natural tick and insect repellent, BIOUD, as a DEET replacement and for use on cotton fabric. Pp. 1006-1016. In: Proc. 2006 Beltwide Cotton Conf., San Antonio Tex.—Jan. 3-6, 2006.

Sutcliffe, J. E. 1994. Sensory bases of attractancy: morphology of mosquito olfactory sensilla—a review. *J. Am. Mosq. Contr. Assoc.* 10: 309-315.

Takken, W., Knols, B. G. J., and Otten, H. 1997. Interactions between physical and olfactory cues in the host-seeking behaviour of mosquitoes: the role of relative humidity. *Annals Trop. Med. Parasitol.* 91: S119-S120.

Tawatsin A., Wratten S. D., Scott, R. R., Thavara, U., Techadamrongsin, Y. 2001. Repellency of volatile oils from plants against three mosquito vectors. *J. Vector Ecol.* 26: 7-82.

Trigg, J. K. 1996. Evaluation of a eucalyptus-based repellent against *Anopheles* spp. in Tanzania. *J. Am. Mosq. Contr. Assoc.* 12: 243-246.

Trongtokit, Y., Rongrisyam, Y., Komalamisra, N., and Apiwathnasorn, C. 2005 Comparative repellency of 38 essential oils against mosquito bites. *Phytother. Res.* 19: 303-309.

Tuetun, B., Choochote, W., Kanjanapothi, D., Rattanchanpichai, E., Chaithong, U., Chaiwong, P., Jitpakdi, A., Tippawangkosol, P., Riying, D., and Pitasawat, B. 2005. Trop. Med. Internat. Health 10: 1190-1198.

Zanotto, P. M. D., Gould, E. A., Gao, G. F., Harvey, P. H., and Holmes, E. C. 1996. Population dynamics of flaviviruses revealed by molecular phylogenies. *Proc. Nat. Acad. Sci. USA.* 93: 548-553.

World Health Organization. 1996. Report of the WHO informal consultation on the evaluation and testing of insecticides. CID/WHOPEWS/IC/96.1. p. 69.

Zwiebel, L. J., and Takken, W. 2004. Olfactory regulation of mosquito-host interactions. *Insect Biochem. Mol. Biol.* 34: 645-652.

What is claimed is:

1. A compound selected from the group consisting of 7-allylsulfanylheptan-n ol, 8-allylsulfanyloctan-n-ol and 9-allylsulfanylnonan-n-ol, wherein n=1-4.

2. A compound selected from the group consisting of 9-allylsulfanylnonan-1-ol, 8-allylsulfanyloctan-1-ol, 7-allylsulfanylheptan-1-ol, 9-allylsulfanylnonan-2-ol, 8-allylsulfany-loctan-2-ol, 7-allylsulfanylheptan-2-ol, 6-allylsulfanylhexan-2-ol, 8-allylsulfanyloctan-3-ol and 8-allylsulfanyloctan-4-ol.

3. The compound 8-allylsulfanyloctan-1-ol.

4. A composition comprising a compound of claim 1 and a carrier.

5. A composition comprising a compound of claim 1 and one or more additional compounds selected from the group consisting of vanillin, 1,8-cineole, linalool, citronellal, citronellol, camphor, menthone, isomenthone, menthol, borneol, isomenthol, α-terpineol, cis- and trans-piperitol, nerol, neral, cinnamaldehyde, cumin aldehyde, geraniol, geranial, thymol, bornyl acetate, menthyl acetate, cumin alcohol, geranyl formate, geranyl acetate, caryophyllene, cis-cinnamyl acetate, N,N-diethyl-m-toluamide, p-menthane-3,8-diol, 2-undecanone, tetrahydronootkatone, 1,10-dihydronootkatone, callicarpenal, and intermedeol.

6. The composition of claim 5 wherein the one or more additional compounds comprises vanillin.

7. A composition comprising a compound of claim 3 and a carrier.

8. A composition comprising a compound of claim 3 and one or more additional compounds selected from the group consisting of vanillin, 1,8-cineole, linalool, citronellal, citronellol, camphor, menthone, isomenthone, menthol, borneol, isomenthol, α-terpineol, cis- and trans-piperitol, nerol, neral, cinnamaldehyde, cumin aldehyde, geraniol, geranial, thymol, bornyl acetate, menthyl acetate, cumin alcohol, geranyl formate, geranyl acetate, caryophyllene, cis-cinnamyl acetate, N,N-diethyl-m-toluamide, p-menthane-3,8-diol, 2-undecanone, tetrahydronootkatone, 1,10-dihydronootkatone, callicarpenal, and intermedeol.

9. The composition of claim 8 wherein the one or more additional compounds comprises vanillin.

10. A method for repelling blood-feeding ectoparasitic arthropods from a location to be protected therefrom, the method comprising applying to the location a compound of claim 1.

11. The method of claim 10, wherein the blood-feeding ectoparasitic arthropods comprise insects of the Order Diptera in the Families Culicidae, Tabanidae, Psychodidae, Simuliidae, Muscidae, and Ceratopogonidae.

12. The method of claim 11, wherein the insects in the family Culicidae comprise species in the genera *Aedes, Culex, Anopheles, Chagasia, Bironella, Culiseta, Psorophora, Toxorhynchites, Mansonia,* and *Coquillettidia*.

13. The method of claim 12, wherein the species is selected from the group consisting of *Aedes aegypti, Anopheles gambiae* and *Culex quinquefasciatus*.

14. The method of claim 10, wherein the compound is applied on a surface of the location at a concentration of between 1 nanogram to 100 milligrams per square centimeter.

15. The method of claim 10, wherein the location is a surface of the skin of a mammal, bird, reptile or amphibian.

16. The method of claim 15, wherein the mammal is a human.

17. A method for repelling blood-feeding ectoparasitic arthropods from a location to be protected therefrom, the method comprising applying to the location a compound of claim 3.

18. The method of claim 17, wherein the blood-feeding ectoparasitic arthropods comprise insects of the Order Diptera in the Families Culicidae, Tabanidae, Psychodidae, Simuliidae, Muscidae, and Ceratopogonidae.

19. The method of claim 18, wherein the insects in the family Culicidae comprise species in the genera *Aedes, Culex, Anopheles, Chagasia, Bironella, Culiseta, Psorophora, Toxorhynchites, Mansonia,* and *Coquillettidia*.

20. The method of claim 19, wherein the species is selected from the group consisting of *Aedes aegypti, Anopheles gambiae* and *Culex quinquefasciatus*.

21. The method of claim 17, wherein the compound is applied on a surface of the location at a concentration of between 1 nanogram to 100 milligrams per square centimeter.

22. The method of claim 17, wherein the location is a surface of the skin of a mammal, bird, reptile or amphibian.

23. The method of claim 22, wherein the mammal is a human.

* * * * *